US012751992B2

(12) United States Patent
Puri et al.

(10) Patent No.: US 12,751,992 B2
(45) Date of Patent: Oct. 6, 2026

(54) METHODS AND COMPOSITIONS FOR TREATING CARDIOVASCULAR DISEASES USING FAT SPECIFIC PROTEIN 27 (FSP27) COMPOSITIONS

(71) Applicants: Ohio University, Athens, OH (US); Trustees of Boston University, Boston, MA (US)

(72) Inventors: Vishwajeet Puri, Athens, OH (US); John J. Kopchick, Athens, OH (US); Vishva Sharma, Athens, OH (US); Noyan Gokce, Athens, OH (US); Shakun Karki, Athens, OH (US)

(73) Assignees: Ohio University, Athens, OH (US); Trustees of Boston University, Boston, MA (US)

( * ) Notice: Subject to any disclaimer, the term of this patent is extended or adjusted under 35 U.S.C. 154(b) by 0 days.

(21) Appl. No.: 18/147,213

(22) Filed: Dec. 28, 2022

(65) Prior Publication Data

US 2023/0338467 A1 Oct. 26, 2023

Related U.S. Application Data

(62) Division of application No. 17/261,822, filed as application No. PCT/US2019/042947 on Jul. 23, 2019, now abandoned.

(60) Provisional application No. 62/703,216, filed on Jul. 25, 2018.

(51) Int. Cl.

| | |
|---|---|
| ***A61K 38/17*** | (2006.01) |
| ***A61K 45/06*** | (2006.01) |
| ***C07K 14/435*** | (2006.01) |

(52) U.S. Cl.
CPC .......... *A61K 38/1709* (2013.01); *A61K 45/06* (2013.01); *C07K 14/435* (2013.01)

(58) Field of Classification Search
None
See application file for complete search history.

(56) References Cited

U.S. PATENT DOCUMENTS

| | | | | |
|---|---|---|---|---|
| 2003/0092116 | A1* | 5/2003 | Chun | G01N 33/574 435/69.1 |
| 2003/0124113 | A1* | 7/2003 | Hillman | C07K 14/4747 424/94.63 |
| 2013/0115220 | A1* | 5/2013 | Miyazaki | A61K 31/713 424/145.1 |
| 2020/0179483 | A1* | 6/2020 | Puri | A61K 38/1709 |
| 2020/0222502 | A1* | 7/2020 | Kopchick | A61P 35/00 |

OTHER PUBLICATIONS

Grahn "Fat-specific Protein 27 (FSP27) Interacts with Adipose Triglyceride Lipase (ATGL) to Regulate Lipolysis and Insulin Sensitivity in Human Adipocytes" The Journal of Biological Chemistry. Mar. 13, 2014: vol. 289. No. 17: pp. 12029-12039.*

* cited by examiner

*Primary Examiner* — Maury A Audet
(74) *Attorney, Agent, or Firm* — MacMillan, Sobanski & Todd, LLC

(57) ABSTRACT

FSP27 compositions and methods for treating cardiovascular diseases are described.

4 Claims, 31 Drawing Sheets
(18 of 31 Drawing Sheet(s) Filed in Color)
Specification includes a Sequence Listing.

| Table 1 | | | | |
|---|---|---|---|---|
| SEQ ID | CF # | Amino acid positions | Peptide length | Peptide Sequence |
| 1 | CF1 | aa 1-60 | 60 | MEYAMKSLSLLYPKSLSRHVSVRTSVVTQQLLSEPSPKAPR ARPCRVSTADRSVRKGIMA |
| 2 | CF2 | aa 173-220 | 48 | YDLHCCGAKRIMKEAFRWALFSMQATGHVLLGTSCYLQQLL DATEEGQ |
| 3 | CF3 | aa 40-120 | 81 | PRARPCRVSTADRSVRKGIMAYSLEDLLLKVRDTLMLADKP FFLVLEEDGTTVETEEYFQALAGDTVFMVLQKGQKWQPPS |
| 4 | CF4 | aa 120-140 | 21 | SEQGTRHPLSLSHKPAKKIDV |
| 5 | CF5 | aa 210-220 | 11 | QQLLDATEEGQ |
| 6 | CF6 | aa 210-239 | 29 | QQLLDATEEGQPPKGKASSLIPTCLKILQ |
| 7 | CF7 | aa 120-239 | 120 | SEQGTRHPLSLSHKPAKKIDVARVTFDLYKLNPQDFIGCLNV KATFYDTYSLSYDLHCCGAKRIMKEAFRWALFSMQATGHVL LGTSCYLQQLLDATEEGQPPKGKASSLIPTCLKILQ |
| 8 | CF8 | aa 120-130 | 11 | SEQGTRHPLSL |
| 9 | CF9 | aa 120-210 | 91 | SEQGTRHPLSLSHKPAKKIDVARVTFDLYKLNPQDFIGCLNV KATFYDTYSLSYDLHCCGAKRIMKEAFRWALFSMQATGHVL LGTSCYLQ |
| 10 | CF10 | aa 120-220 | 101 | SEQGTRHPLSLSHKPAKKIDVARVTFDLYKLNPQDFIGCLNV KATFYDTYSLSYDLHCCGAKRIMKEAFRWALFSMQATGHVL LGTSCYLQQLLDATEEGQ |
| 11 | CF11 | aa 140-210 | 71 | VARVTFDLYKLNPQDFIGCLNVKATFYDTYSLSYDLHCCGAK RIMKEAFRWALFSMQATGHVLLGTSCYLQ |
| 12 | CF12 | Aa 1-238 | 238 | MEYAMKSLSLLYPKSLSRHVSVRTSVVTQQLLSEPSPKAPR ARPCRVSTADRSVRKGIMAYSLEDLLLKVRDTLMLADKPFFL VLEEDGTTVETEEYFQALAGDTVFMVLQKGQKWQPPSEQG TRHPLSLSHKPAKKIDVARVTFDLYKLNPQDFIGCLNVKATFY DTYSLSYDLHCCGAKRIMKEAFRWALFSMQATGHVLLGTSC YLQQLLDATEEGQPPKGKASSLIPTCLKILQ |

FIG. 17

METHODS AND COMPOSITIONS FOR TREATING CARDIOVASCULAR DISEASES USING FAT SPECIFIC PROTEIN 27 (FSP27) COMPOSITIONS

CROSS-REFERENCE TO RELATED APPLICATIONS

This application is a divisional application of U.S. patent application Ser. No. 17/261,822 filed Jan. 20, 2021, still pending, which is a national stage application filed under 35 U.S.C. § 371 of international application PCT/US2019/042947 filed Jul. 23, 2019, filed under the authority of the Patent Cooperation Treaty, which claims priority to U.S. Provisional Application Ser. No. 62/703,216 filed Jul. 25, 2018, the entire disclosures of which are expressly incorporated herein by reference.

STATEMENT REGARDING FEDERALLY SPONSORED RESEARCH

This invention was made with government support under R01 HL140836 awarded by National Institutes of Health. The government has certain rights in the invention.

SEQUENCE LISTING

The instant application contains a Sequence Listing which has been submitted electronically in XML format and is hereby incorporated by reference in its entirety. Said XML copy, created on Apr. 5, 2023 is named 63857-US-PC-D_OU-18013-DIV_SL.xml and is 20,077 20.262 bytes in size.

BACKGROUND OF THE INVENTION

Insulin resistance and cardiovascular diseases are associated disorders, the incidence of which is increasing worldwide. Millions of obese adults at major risk for diabetes and cardiovascular disease. Despite reductions in preventable global health risks such as tobacco and malnutrition, obesity has persisted with recent World Health Organization data showing that not a single country has been able to reverse obesity trends over the past 33 years and more and more Americans are giving up trying to lose weight. Cardiovascular disease is the leading cause of death in these populations and strategies to reverse cardiometabolic risk are urgently needed.

The endothelium plays a critical role in vascular homeostasis and many of its functions are governed by the basal and stimulated release of endothelium-derived nitric oxide (NO) that maintains arterial tone, inhibits inflammation, promotes fibrinolysis, and modulates reparative angiogenesis. Animal and clinical studies show that insulin resistance not only perturbs metabolic pathways in organs such as liver, fat, and muscle, but also negatively influences the vasculature. Insulin normally regulates blood flow through activation of endothelial NO synthase (eNOS) by binding to its IRS-1-linked receptor with subsequent phosphorylation and activation of eNOS via PI3-K/Akt. Defective insulin signaling leads to vascular inflammation, vasoconstriction, plaque progression and ischemia, and endothelium-specific deletion of the insulin receptor in animals causes profound atherosclerosis.

Further, elevated concentrations of circulating free fatty acids (FFAs) and triglycerides (TGs) are central features of insulin resistance that are associated with lipotoxicity and systemic endothelial dysfunction.

The lack of therapeutic options and only limited effects of available drugs, creates a huge challenge in cardiovascular disease therapy.

Thus, there is a great medical need for life-saving treatments for the millions of patients suffering from cardiovascular diseases.

There is no admission that the background art disclosed in this section legally constitutes prior art.

SUMMARY OF THE INVENTION

In a first broad aspect, described herein are uses of FSP27 compositions. It is now described herein that the exogenous delivery of FSP27 is able to rescue FSP27 dysfunction or augment the endogenous function of FSP27.

In another broad aspect, described herein are methods of treatment where administering exogenous recombinant FSP27 (rFSP27) as a therapeutic for the treatment of human cardiovascular diseases.

Such uses include, but are not limited to, increasing levels of FSP27 in a subject by administering exogenous recombinant FSP27 (rFSP27).

In certain embodiments, one fragment of FSP27 is comprised of amino acids 120-140.

Described herein are examples showing the activity of exogenously administered human FSP27 and peptide fragments or analogs in human cardiovascular diseases.

In another broad aspect, described herein are pharmaceutical compositions comprising one or more FSP27 medicaments. FSP27 medicaments may be administered as a pharmaceutically acceptable salt, or as a pegylated composition, or be modified in a pharmaceutically acceptable manner so as to improve the therapeutic properties. FSP27 medicaments may also be administered optionally together with one or more inert carriers and/or diluents.

The FSP27 medicament is present in an amount sufficient to treat one or more types of cardiovascular disease.

In another broad aspect, described herein is a method of treating a subject, the method comprising: administering a composition comprising a nucleic acid encoding a FSP27 protein or a fragment thereto a subject; wherein, the FSP27 protein has an amino acid sequence having greater than 85% homology to at least one of the FSP27 or the FSP27 fragments shown.

In certain embodiments, the FSP27 protein has an amino acid sequence having greater than about 90% homology to the FSP27 sequences.

In certain embodiments, the FSP27 protein has an amino acid sequence having greater than about 95% homology to the FSP27 sequences.

In certain embodiments, the FSP27 protein has an amino acid sequence having greater than about 99% homology to the FSP27 sequences.

In certain embodiments, the FSP27 protein is naturally occurring.

In certain embodiments, the FSP27 protein is a recombinant protein.

In certain embodiments, the FSP27 protein comprises a core FSP27 domain, such as amino acids comprising: aa120-239 of FSP27; aa120-230 of FSP27; aa120-210; aa120-140; aa120-220; aa140-210; and/or aa173-220 of FSP27.

In certain embodiments, the subject is a human.

In certain embodiments, the nucleic acid encoding the FSP27 protein is operably linked to a constitutive transcriptional regulatory sequence containing a variety of control elements such as promoters, enhancers, silencers and the like (hereafter collectively called a promoter), an adipocyte-specific promoter, or an inducible promoter.

In certain embodiments, the composition comprises a plasmid, the plasmid comprising the nucleic acid encoding the FSP27 protein operably linked to a promoter.

In certain embodiments, the composition comprises a viral vector, the viral vector comprising the nucleic acid encoding the FSP27 protein operably linked to a promoter.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A—Treatment of visceral fat with rFSP27 decreased basal lipolysis. FIG. 4B—Recombinant FSP27 increased Akt and eNOS activity (phosphorylation) in adipose tissue. Quantification of insulin-stimulated Akt (FIG. 4C) and eNOS (FIG. 4D) activation in fat. Data are presented as ±SEM. (n=10, *p<0.05).

FIG. 5A—Knockdown of FSP27 in subcutaneous adipose tissue increased rate of glycerol release in the media. Data are presented as ±SEM. (n=7, *p<0.01); FIG. 5B—siRNA-mediated FSP27 depletion decreased Akt and eNOS phosphorylation in response to insulin.

FIG. 7A: Co-IP of FSP27 with VEGF-A in endothelial cells; FIG. 7B; IVTT of FSP27 and VEGF-A.

FIG. 8A: Almost complete loss of FSP27 was observed in clones #3, 7 and 15; FIG. 8B; these cells had markedly blunted insulin-stimulated AKt phosphorylation.

FIGS. 9A-9B display examples of quantitative immunofluorescence images, demonstrating normal p-eNOS stimulation to insulin; FIG. 9C, insulin activation of eNOS at Ser1177 is markedly blunted in endothelial cells (EC's) isolated from visceral compared to SC fat.

FIGS. 13A-13C: Generation of FSP27tg mice. Schematic representation of generation of: (FIG. 13A) adipose tissue specific (Ad-FSP27tg), and (FIG. 13B) Endothelial specific (E-FSP27tg) human-FSP27 (hFSP27) expressing transgenic mice. (FIG. 13C) Genotyping results of F1 pups containing hFSP27 transgene (Ln 1 and 2).

FIG. 17: Table 1, showing the amino acid sequence detail of the relevant peptides, listing SEQ ID NOs: 1-12.

FIG. 20A-2B: Increased oxygen consumption in E-hFSP27tg mice compared to FSP27-floxed (Control) mice. At the age of 4 months these mice were fed 60% high-fat diet for 2 months.

DETAILED DESCRIPTION OF THE PREFERRED EMBODIMENT(S)

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Definitions

In order to facilitate review of the various embodiments of the disclosure, the following explanations of specific terms are provided:

FSP27: Refers to Fat Specific Protein 27, as well as any other accepted nomenclature for the gene in human or other non-human species, including but not limited to CIDEC, Cidec, Cide-C, and Cide-3.

FSP27 Compositions/Medicaments: Refers to the FSP27 as shown in the schematic representation of FSP27 fragments, the amino acids, and the amino acid sequences listed in FIGS. 14-17, including any substitutions, deletions, modifications, or mutations thereof.

Figure 16:
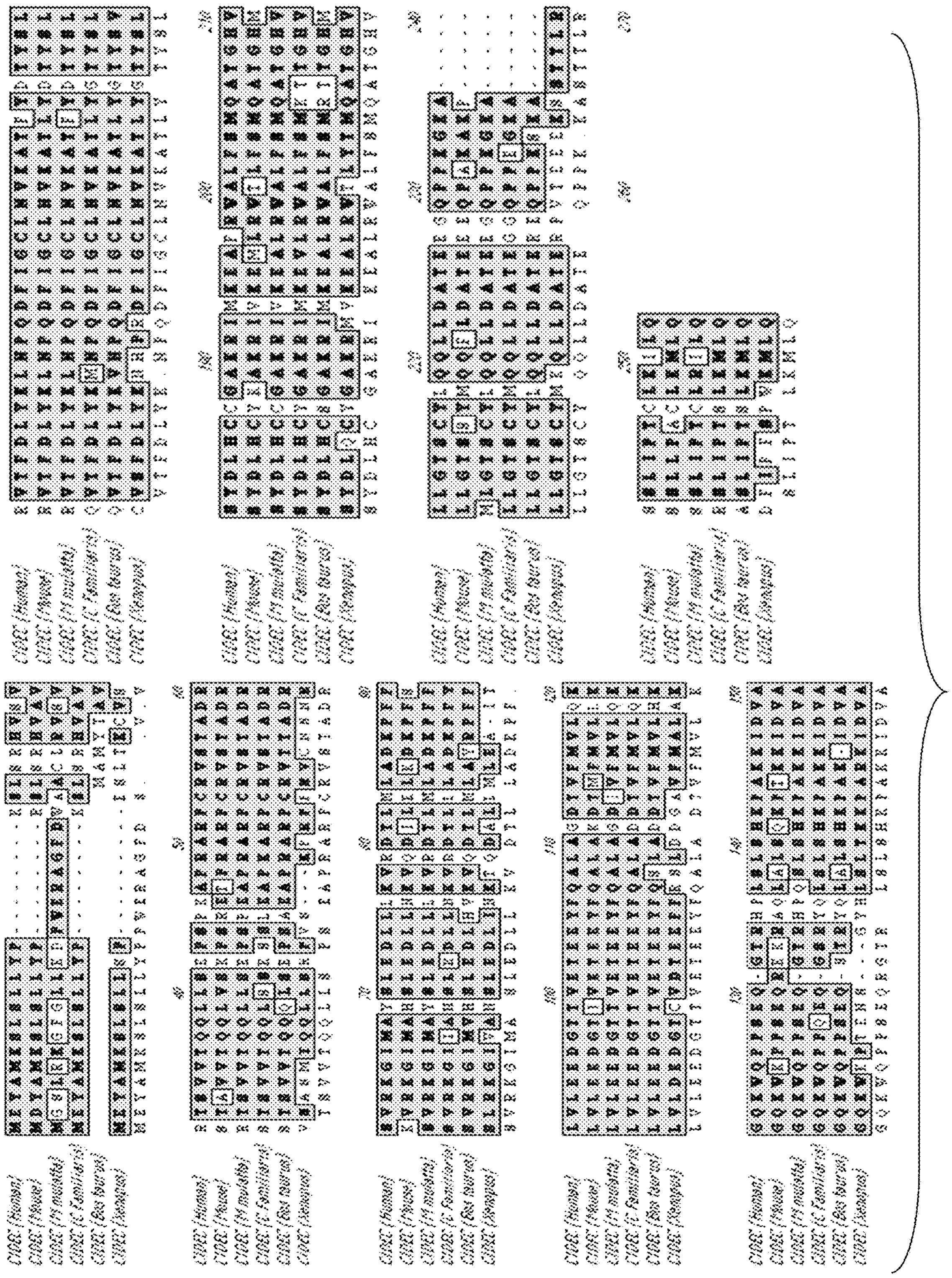
FIG. 16: FSP27 sequence is conserved in vertebrates; for example, >90% conserved sequence in FSP27 in: humans (SEQ ID NO: 12); mouse (SEQ ID NO: 13); monkey (SEQ ID NO: 14); dog (SEQ ID NO: 15); cow (SEQ ID NO: 16); and, frog (SEQ ID NO: 17).

FSP27 Compositions/Medicaments as contemplated herein may also be prepared as recombinant proteins, including the FSP27 sequences shown in FIG. 16, and in Table 1 in FIG. 17.

The FSP27 protein is encoded by a nucleic acid sequence or gene. As used herein, a "nucleic acid" or "polynucleotide" includes a nucleic acid, an oligonucleotide, a nucleotide, a polynucleotide, and any fragment or variant thereof. The nucleic acid or polynucleotide may be double-stranded, single-stranded, or triple-stranded DNA or RNA (including cDNA), or a DNA-RNA hybrid of genetic or synthetic origin, wherein the nucleic acid contains any combination of deoxyribonucleotides and ribonucleotides and any combination of bases, including, but not limited to, adenine, thymine, cytosine, guanine, uracil, inosine, and xanthine hypoxanthine. The nucleic acid or polynucleotide may be combined with a carbohydrate, lipid, protein, or other materials. Preferably, the nucleic acid encodes FSP27 protein.

The "complement" of a nucleic acid refers, herein, to a nucleic acid molecule with sufficient homology to recognize, or which will hybridize to another nucleic acid under conditions of high stringency. High-stringency conditions are known in the art (see e.g., Maniatis et al., Molecular Cloning: A Laboratory Manual, 2nd ed. (Cold Spring Harbor: Cold Spring Harbor Laboratory, 1989) and Ausubel et al., eds., Current Protocols in Molecular Biology (New York, N.Y.: John Wiley & Sons, Inc., 2001)). Stringent conditions are sequence-dependent, and may vary depending upon the circumstances. As used herein, the term "cDNA" refers to an isolated DNA polynucleotide or nucleic acid molecule, or any fragment, derivative, or complement thereof. It may be double-stranded, single-stranded, or triple-stranded, it may have originated recombinantly or synthetically, and it may represent coding and/or noncoding 5' and/or 3' sequences.

In addition, "complementary" means not only those that are completely complementary to a region of at least 15 continuous nucleotides, but also those that have a nucleotide sequence homology of at least 40% in certain instances, 50% in certain instances, 60% in certain instances, 70% in certain instances, at least 80%, 90%, and 95% or higher. The degree of homology between nucleotide sequences can be determined by various methods, including an algorithm, BLAST, etc.

As used herein, nucleic acids and/or nucleic acid sequences are "homologous" when they are derived, naturally or artificially, from a common ancestral nucleic acid or nucleic acid sequence. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95%, 96%, 97%, 98%, or 99% or more can also be used to establish homology. Methods for determining sequence similarity percentages (e.g., BLASTN using default parameters) are generally available. Software for performing BLAST analyses is publicly available through the National Center for Biotechnology Information.

The nucleic acid agent, for example, may be a plasmid. Such a plasmid may comprise a nucleic acid sequence encoding FSP27, variants or isoforms thereof, although it is to be understood that other types of nucleic acid agents, such as recombinant viral vectors, may also be used for the purposes of the present invention. In one embodiment of the present invention, the nucleic acid (e.g., plasmid) encodes at least one FSP27 variant or isoform.

The term "plasmid", as used herein, refers generally to circular double-stranded DNA, which is not bound to a chromosome. The DNA, for example, may be a chromosomal or episomal-derived plasmid. The plasmid of the present invention may optionally contain an initiator or promoter of transcription, terminator of transcription, translational control sequences, and/or a discrete series of restriction-endonuclease recognition sites, located between the promoter and the terminator. In the plasmid, a polynucleotide insert of interest (e.g., one encoding a FSP27-associated protein) should be operatively linked to an appropriate promoter. The promoter may be its native promoter or a host-derived promoter. The promoter may also be a tissue-specific promoter, such as an adipocyte-specific promoter or other tissue-specific promoter. The promoter may further be a regulatable promoter, which may be turned off when the expression of the gene is no longer desired. Non-limiting examples of promoters for use in the present invention include the actin promoter and viral promoters. Other suitable promoters will be known to the skilled artisan.

Therapeutic: A generic term that includes both diagnosis and treatment. It will be appreciated that in these methods the "therapy" may be any therapy for treating a disease including, but not limited to, pharmaceutical compositions, gene therapy and biologic therapy such as the administering of antibodies and chemokines. Thus, the methods described herein may be used to evaluate a patient or subject before, during and after therapy, for example, to evaluate the reduction in disease state.

Adjunctive therapy: A treatment used in combination with a primary treatment to improve the effects of the primary treatment.

Clinical outcome: Refers to the health status of a patient following treatment for a disease or disorder or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Decrease in survival: As used herein, "decrease in survival" refers to a decrease in the length of time before death of a patient, or an increase in the risk of death for the patient.

Patient: As used herein, the term "patient" includes human and non-human animals. The preferred patient for treatment is a human. "Patient," "Individual" and "subject" are used interchangeably herein.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Poor prognosis: Generally refers to a decrease in survival, or in other words, an increase in risk of death or a decrease in the time until death. Poor prognosis can also refer to an increase in severity of the disease.

Screening: As used herein, "screening" refers to the process used to evaluate and identify candidate agents that affect such disease.

Comprising, comprises and comprised of: As used herein are synonymous with "including", "includes" or "containing", "contains", and are inclusive or open-ended and do not exclude additional, non-recited members, elements or method steps. The terms "comprising", "comprises" and "comprised of" also include the term "consisting of".

About: As used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

And/or: When used in a list of two or more items, means that any one of the listed items can be employed by itself or any combination of two or more of the listed items can be employed. For example, if a list is described as comprising group A, B, and/or C, the list can comprise A alone; B alone; C alone; A and B in combination; A and C in combination, B and C in combination; or A, B, and C in combination.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Fat Specific Protein (FSP27), also known as cell death-inducing DFFA-like effector (CIDEC in humans and Cidec in mice; also abbreviated Cide-c or Cide-3) is a member of the cell death-inducing DNA fragmentation factor-like effector family—a group of genes that play an important role in apoptosis. The invention described herein identifies an additional, novel role of FSP27 as a therapeutic target for treating cardiovascular disease.

It is now shown herein that FSP27 protein increases eNOS activity (which is a marker of vascular function).

It is also now shown herein that FSP 27 is abundantly expressed in vascular endothelial cells in intracellular network formations completely different than in adipocytes, and is down-regulated particularly in association with visceral obesity. It is now believed that perturbations in FSP27 promote conditions that elevate FFAs which are implicated in insulin resistance and endothelial dysfunction. While lipid storage or breakdown is generally not viewed as a primary function of vascular endothelial cells, it is now believed that FSP27 governs cellular responses by mechanisms beyond regulation of lipid metabolism, such as by modulating signal transduction or functioning as a chaperone co-receptor for other proteins. While no wishing to be bound by theory, it is also now believed that FSP27 serves as a critical regulator of arteriolar vasodilator capacity and angiogenesis which are pivotal in mechanisms of atherosclerosis and ischemic cardiovascular disease. Non-limiting examples of cardiovascular diseases include one or more of the following: cardiovascular conditions: ischemic heart disease, coronary artery disease (CAD), angina, infarction, coronary syndrome, peripheral artery disease (PAD), cerebrovascular disease, stroke, congestive heart failure, systolic or diastolic cardiomyopathy, insulin resistance, vascular spasm, vasospastic angina, cardiac arrhythmia, impaired angiogenesis, reduced vascular growth.

The domains and/or sequences of the FSP27 protein and rFSP27 are useful as peptides to protect epithelial cells against insulin resistance and cardiovascular disease.

Figure 1:
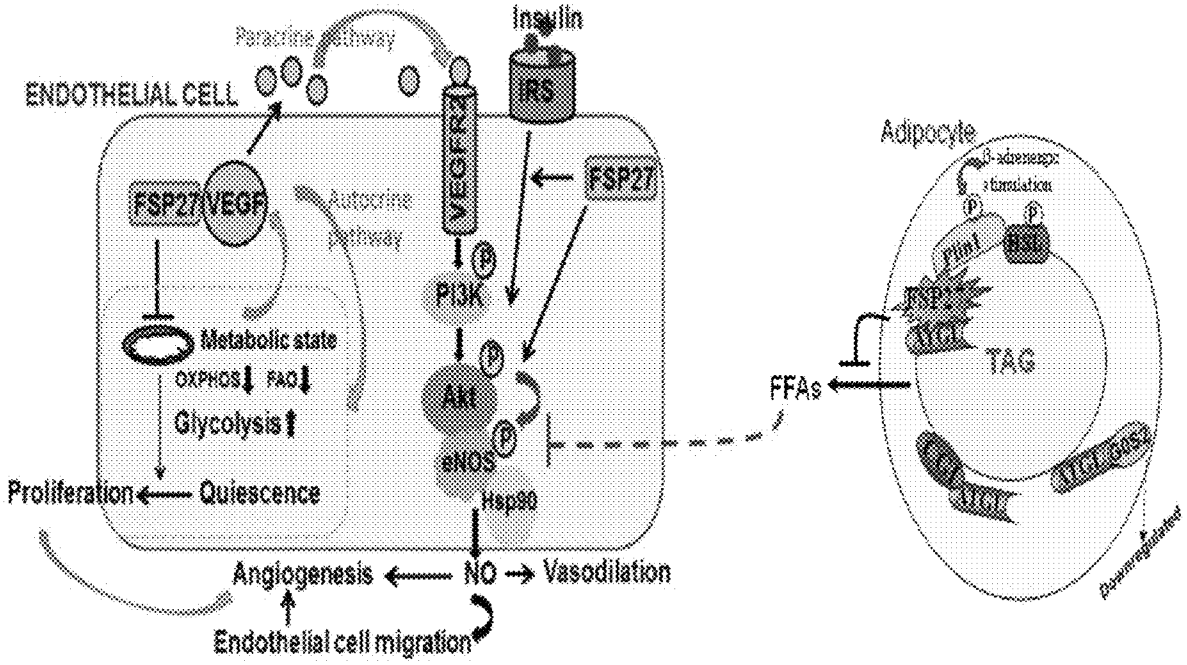
FIG. 1: Schematic illustration of two distinct pathways: left) endothelial cell-specific FSP27 regulation of eNOS signaling and angiogenesis via potential interaction with VEGF; and, right) adipocyte-specific FSP27 regulation of cross-talk with endothelial cells via FFA flux as determinants of vascular phenotype.

FIG. 1 is a schematic illustration of FSP27 and its intricate signaling system which is a previously unrecognized but functionally significant modulator of vascular phenotype.

Figure 2:
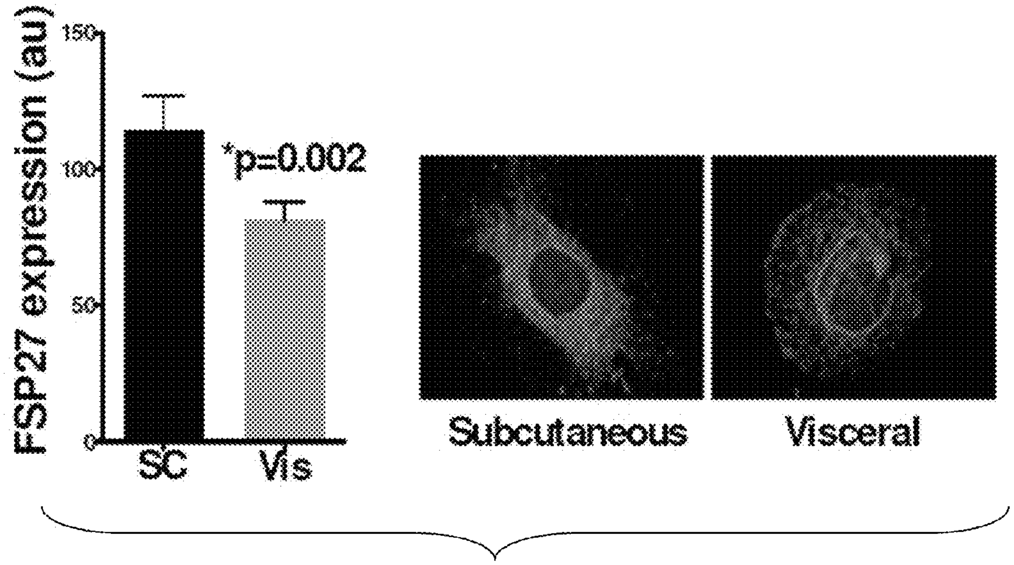
FIG. 2: FSP27 expression in endothelial cells: FSP27 was distributed throughout the cytoplasm, and significantly lower in endothelial cells isolated from visceral vs. subcutaneous depots of obese subjects (n=10, BMI 43±4 kg/m2, *p=0.002; green color=FSP27).

FSP27 is highly expressed in human endothelial cells derived from the adipose tissue microvasculature. As shown in FIG. 2, using immunohistochemistry and confocal imaging, FSP27 protein was clearly detectable and significantly lower in endothelial cells isolated from visceral compared to subcutaneous depots of obese subjects. This is a surprising finding because endothelial cells are generally not considered primary storage sites for lipid metabolism. It is now believed that FSP27 has an alternative function in vascular cells—such as modulation of signal transduction. Also, see FIGS. 10B-10C which show endothelium-specific FSP27 expression, which was knocked-out using CRISPR/Cas9, thereby showing FSP27's cell autonomous role.

It was also determined whether there are any direct effects of FSP27 on vascular responses by examining the effects of human recombinant protein (rFSP27). The primary readout for vascular function involved two key physiological functions of blood vessels: A) endothelium-dependent vasodilation to insulin (as an index of vascular insulin resistance) and B) angiogenic growth capacity (a marker of capillary regenerative potential). Both of these parameters become dysfunctional under disease conditions and contribute to mechanisms of adipose tissue dysfunction locally, and atherosclerosis and ischemic injury systemically.

Figure 3:
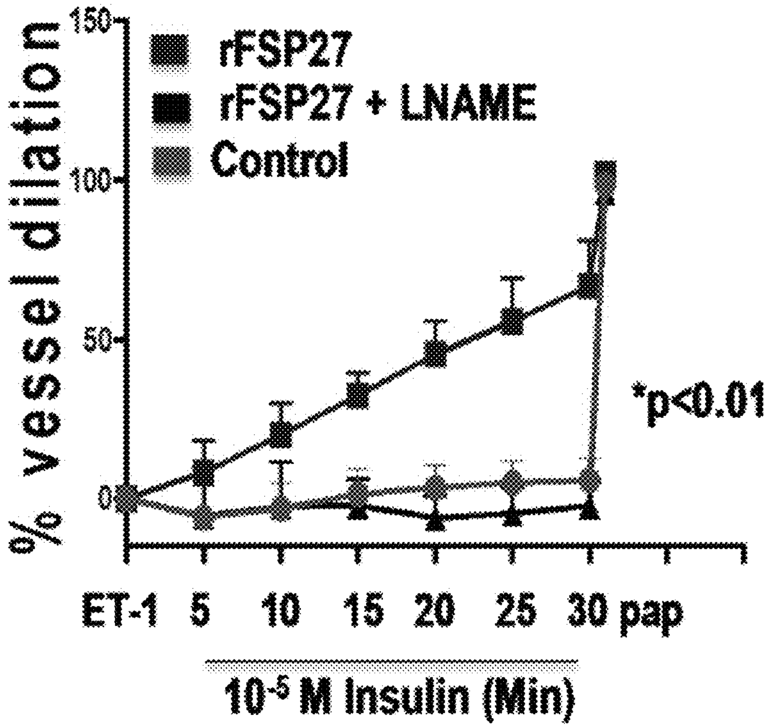
FIG. 3: Vasodilation to insulin improves with rFSP27 (n=10, *p<0.01).

The endothelium-dependent arteriolar vasodilator function of the microvasculature within human adipose tissue was examined using video-microscopy. As shown in FIG. 3, time-response to insulin-mediated, nitric-oxide mediated vasodilation was severely blunted (red plot) in the visceral adipose tissue microvasculature. Responses to non-endothelium-dependent vasodilation to papavarine were intact indicating a functional defect specifically at the level of the endothelium. Treatment with rFSP27 (blue plot) significantly improved vasomotor function (n=10, $p<0.01$) and the positive response was nearly fully abolished by eNOS inhibitor $N^{\omega}$-nitro-L-arginine methyl ester (L-NAME, 100 μM) showing that the beneficial mechanisms was related primarily to improved NO bioaction. To confirm, whole visceral fat was exposed to rFSP27 and examined eNOS phosphorylation (p-eNOS) at serine 1177, the commonly reported major index of eNOS stimulatory activation in endothelial cells.

Figure 4A:
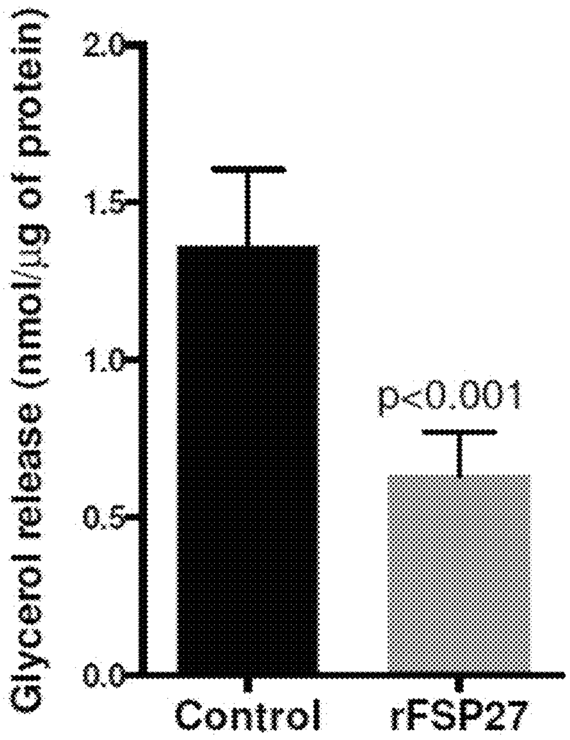
FIGS. 4A-4D: Recombinant FSP27 improves insulin signaling in visceral adipose.
Figure 4B:
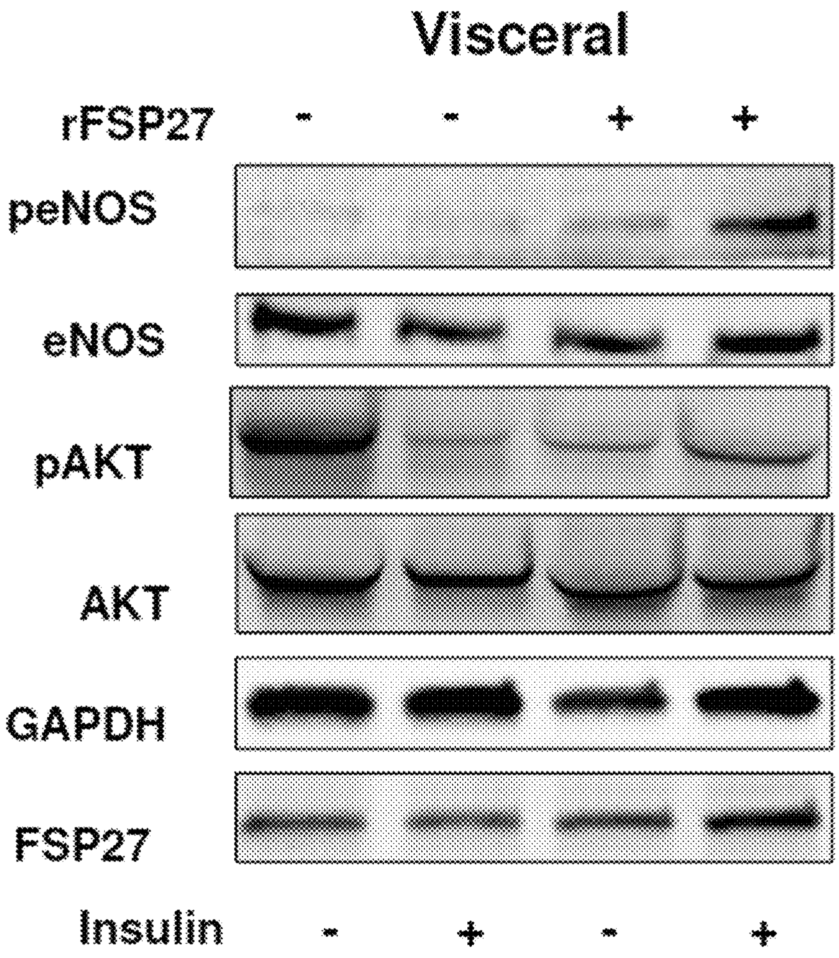
Figure 4C:
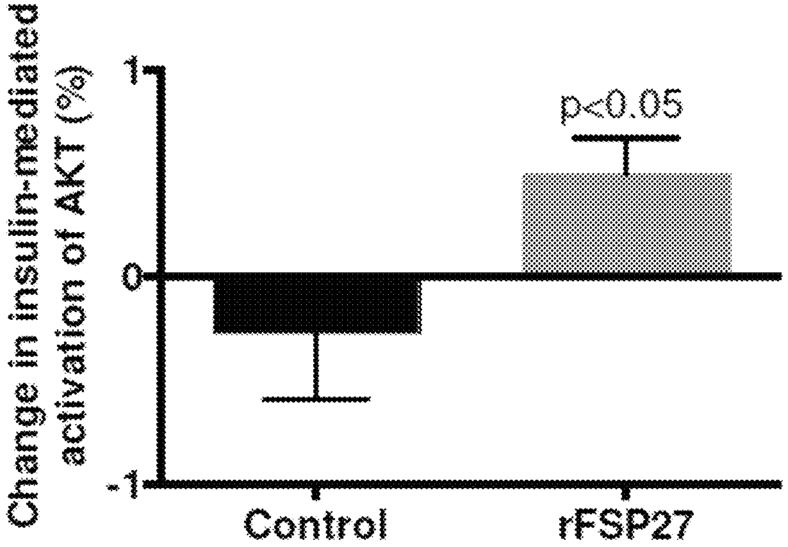
Figure 4D:
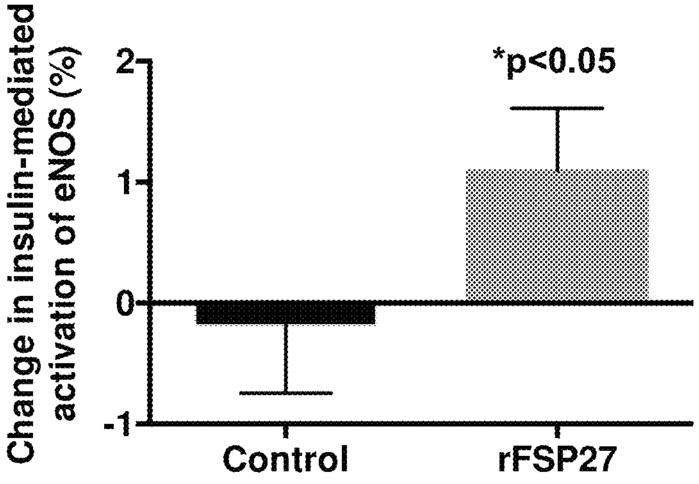

As shown in FIGS. 4A-4D, rFSP27 reduced basal lipolysis (FIG. 4A) and markedly improved insulin-mediated Akt and eNOS activation/phosphorylation (FIGS. 4B-4D) in the visceral fat of obese humans. In particular, FIG. 4D shows the insulin-mediated activation of eNOS and AKT in response to recombinant human FSP27 in the visceral depot, and the quantification of percent change in insulin-mediated activation of eNOS at baseline and after 24 hours of treatment with rFSP27 in the visceral depot. (n=10, $p<0.05$). Data are presented as arbitrary units (au) and as mean±SEM. * $p\leq 0.05$.

Figure 5A:
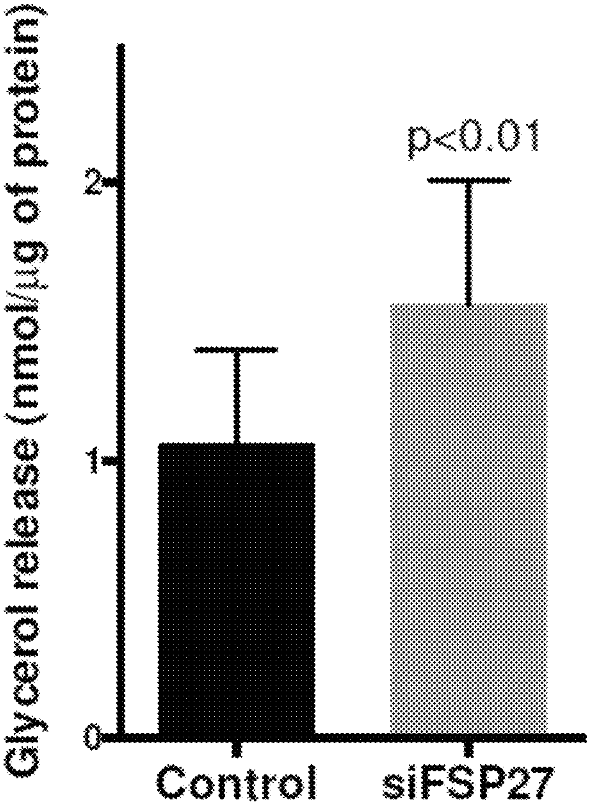
FIGS. 5A-5B: siRNA-mediated FSP27 knockdown increases lipolysis and impairs insulin signaling.
Figure 5B:
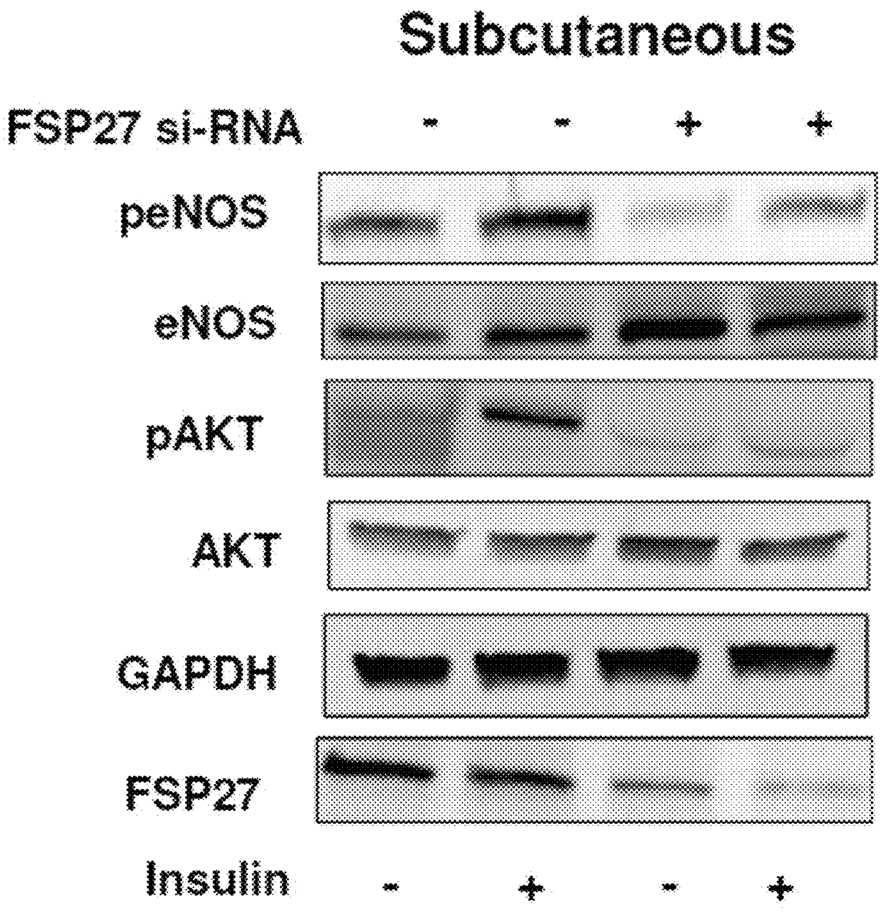

These findings strongly complement the intact vessels physiological studies shown in FIG. 3. Conversely, siRNA methods were used to silence FSP27 (~70% silencing action) in human fat which had opposite effect to rFSP27, and increased lipolysis in parallel with impaired insulin-mediated Akt and eNOS phosphorylation in SC fat (FIGS. 5A-5B).

It was also determined whether FSP27 influences broader functions of blood vessels and specifically focused on angiogenesis. Adipose tissue angiogenesis was examined using ex-vivo Matrigel based assays that examine capillary sprout growth in adipose tissue specimens. Defective angiogenesis in the adipose tissue has been linked to insulin resistance, however mechanisms are unknown. Also, anti-angiogenic mediators produced in human fat are detectable in circulating blood and likely have systemic effects.

Figure 6A:
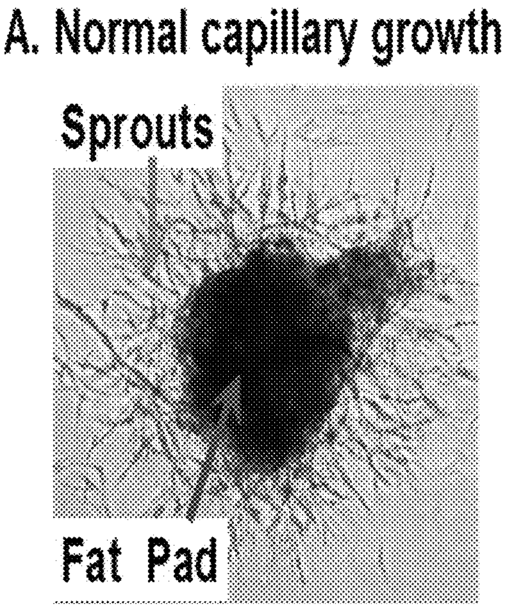
FIGS. 6A-6B: FSP27 enhances in-vitro angiogenic tube formation. Biopsy sample of human adipose fat pads showing normal (FIG. 6A) and blunted (FIG. 6B) capillary grow. FSP27 improves blunted angiogenesis.
Figure 6B:
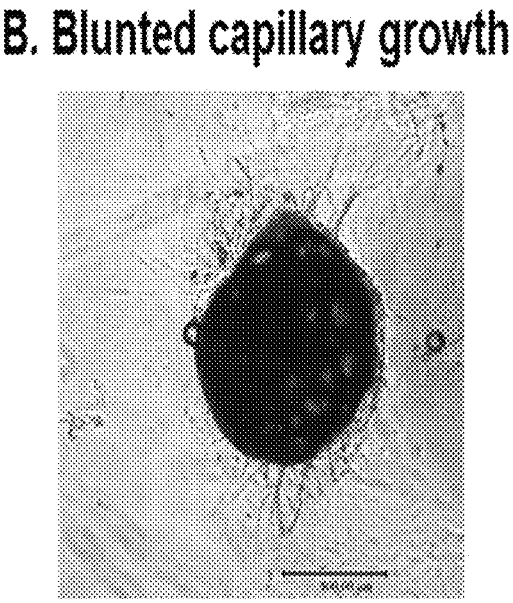
Figure 6C:
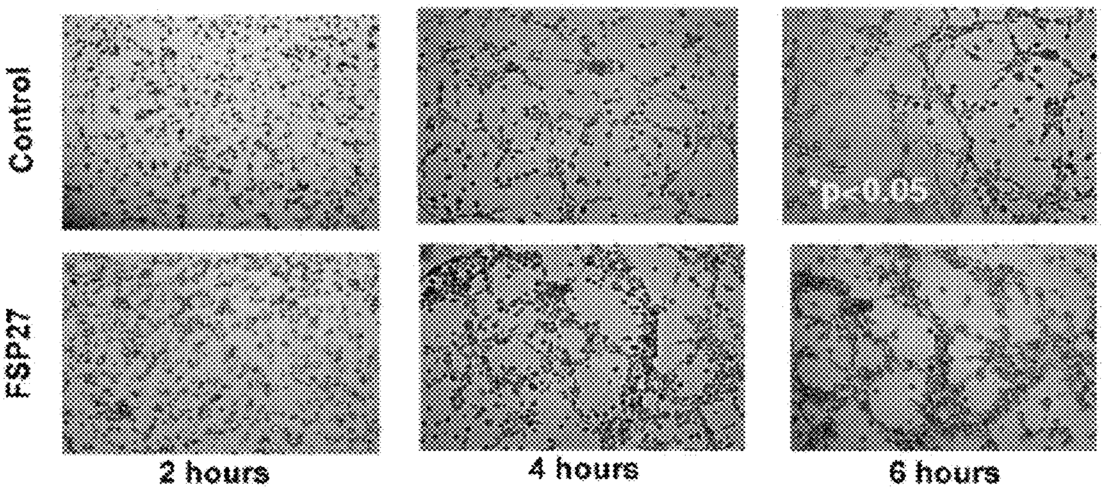
FIG. 6C: FSP27 enhanced angiogenic tube formation within 6 hrs in cultured endothelial cells isolated form the visceral adipose tissue of obese human subjects (BMI 43±4 kg/m2, n=6, p<0.05).

Illustrations of "preserved" and "blunted/abnormal" angiogenic growth in human fat pads are shown in FIGS. 6A-6B. A complimentary method of angiogenic assessment involves a tube formation assay that quantifies the capacity of endothelial cells plated onto gelled basement matrix to organize and coalesce into capillary-like structures with a rudimentary lumen within hours. As shown in FIG. 6C, isolated primary endothelial cells from living obese subjects from the visceral depot exhibited weak vasculogenic behavior (control), whereas rFSP27 significantly improved channel formation at 6 hrs (n=6, *$p<0.05$).

This evidence is striking because FSP27 was initially believed to be exclusively involved in the regulation of adipocyte lipid metabolism. However, these data show that there is a key role and functional significance of FSP27 as a critical endogenous modulator of vascular function in human obesity.

Figure 7A:
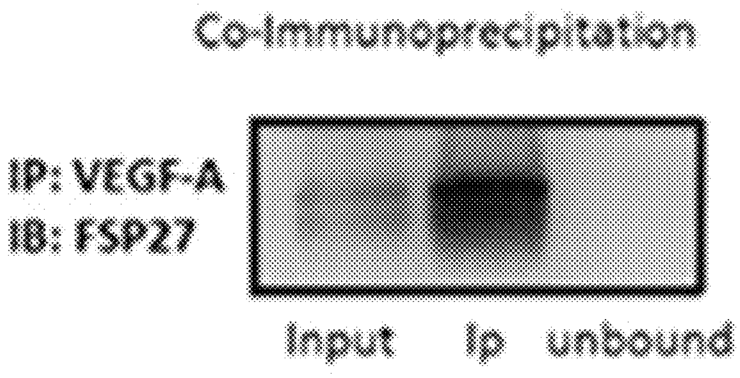
FIGS. 7A-7B: FSP27 interacts directly with VEGF-A.
Figure 7B:
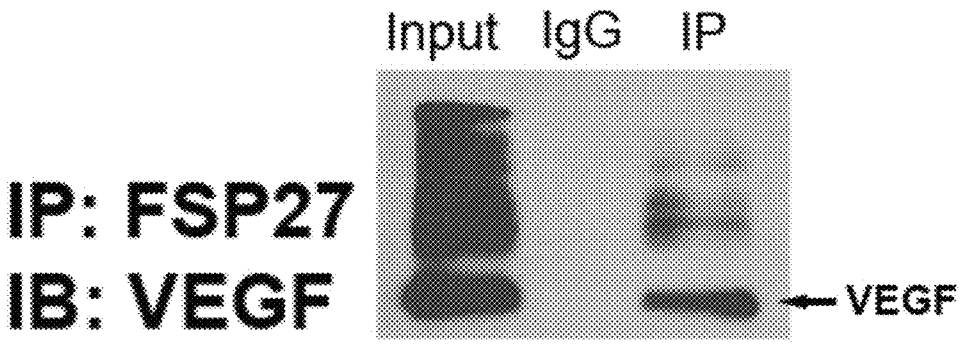

To determine the role of VEGF-A as a candidate mediator of FSP27 action, interaction between these two proteins was examined, a strong co-immunoprecipitation was observed (FIG. 7A). An in vitro transcription-translation coupled co-IP immunoblot assay (IVTT) was conducted which confirmed a direct interaction of FSP27 with VEGF (FIG. 7B). It is now believed that FSP27 functions both at the *nexus* of extracellular signaling via lipotoxicity, and intracellular pathways by interfering with cell-autonomous endothelial responses.

Vascular Cell FSP27 Regulates Angiogenesis Through the VEGF-Akt-eNOS Pathway.

Figure 8A:
FIGS. 8A-8B: Dual RNA CRISPR/Cas9-mediated FSP27 knockout in HUVEC cells.
Figure 8B:
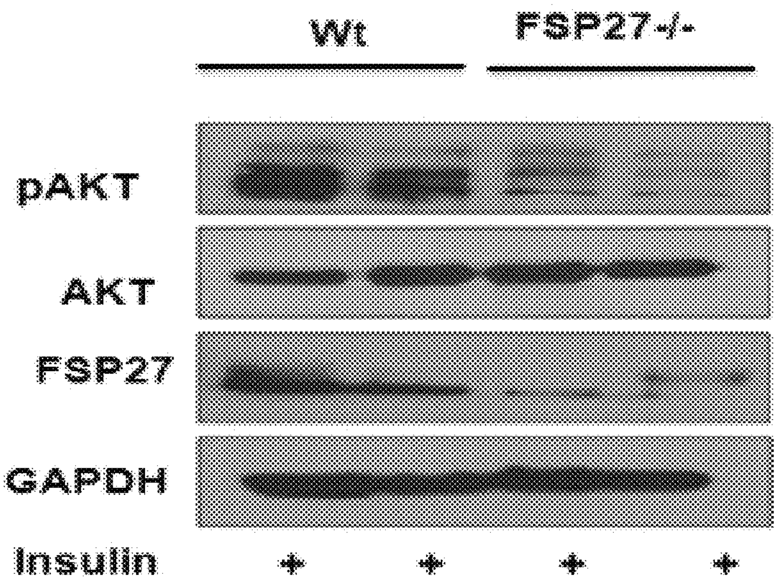

To determine the role of FSP27 in endothelial function, gain-and-loss of function are performed in cultured endothelial cells lines as gene manipulation can be readily performed in these cultured systems. an FSP27 knockout system in human umbilical vein endothelial cell (HUVEC) lines by a du RNA mediated CRISPR/Cas9 method is used, and achieved nearly full loss of FSP27 expression as shown in (FIG. 8A). This produced an approximately 90% decrease in insulin-stimulated Akt phosphorylation (FIG. 8B) showing that FSP27 regulates eNOS activation via Akt signaling.

Also, arterial cell lines (HAECs) and primary endothelial cells that are obtained from different fat depots of human subjects are also examined (as in FIGS. 6A-6C).

As shown in FIG. 1, and data in FIGS. 7A-7B, FSP27-VEGF has autocrine and/or paracrine effects on eNOS activity and angiogenesis.

Angiogenic regulation of FSP27 is determined by blocking intracellular VEGF (autocrine pathway), and extracellular VEGF and VEGFR2 (paracrine pathway). In these experiments, VEGF or VEGFR2 is depleted using RNAi. Further, in order to confirm the role of FSP27-VEGF interactions in vascular modeling, $FSP27^{-/-}$ HAEC cells and use recombinant VEGF are used to determine when the FSP27 is required in the process of eNOS activation and tube formation.

Role of Endothelial-Specific FSP27 in Insulin Signaling in Endothelial Cells.

The activation of eNOS and angiogenesis is dependent upon insulin signaling. The data in FIGS. 4A-D and FIGS. 5A-5B clearly show the effect of FSP27 on eNOS activity and Akt phosphorylation in human adipose tissue. However, the effect of FSP27 on Akt activity could be mainly due to the Akt in adipocytes.

To determine the specific role of FSP27 on insulin signaling via Akt in endothelial cells, the role of FSP27 is investigated in basal and insulin-stimulated Akt activation in HAEC cells in the presence or absence of FSP27, monitored by Akt phosphorylation at $Ser^{473}$ and $Ser^{308}$ sites.

The protocol includes examining eNOS phosphorylation at serine1177 (p-eNOS), the commonly reported major index of eNOS stimulatory activation in endothelial cells.

Figures 9A, 9B:
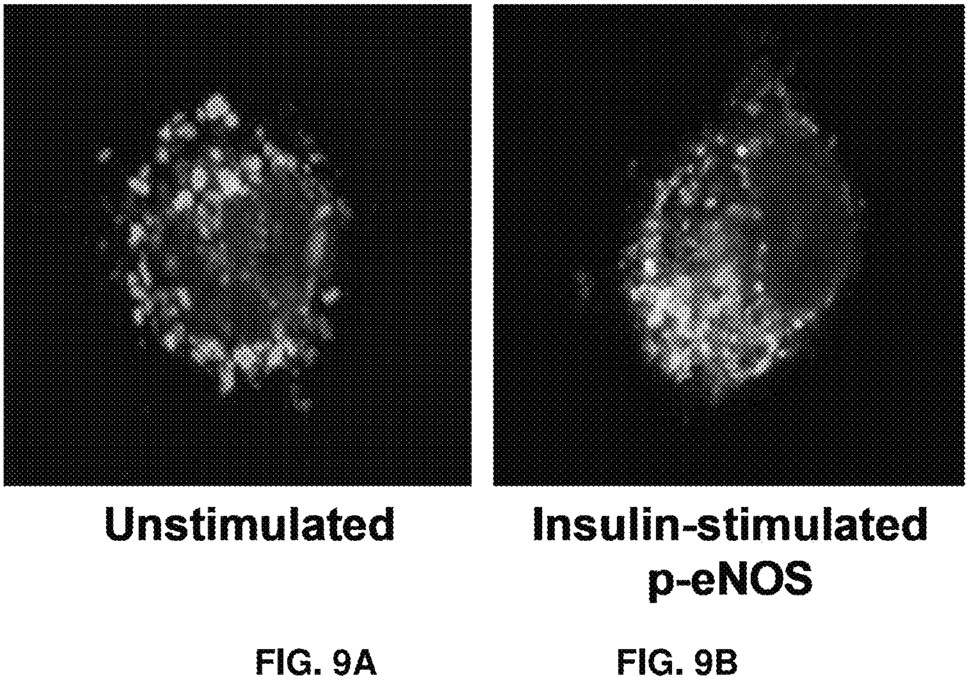
FIGS. 9A-9C: Endothelial cell immunofluorescence, red color, peNOS signal.

FIGS. 9A-9B display examples of quantitative immunofluorescence images, demonstrating normal p-eNOS stimulation to insulin, where the FIG. 9A depicts ambient basal conditions, and FIG. 9B panel shows potent insulin stimulation of p-eNOS at Ser1177 (depicted by intensification of the red signal). DAPI nuclear stain (blue) and von Willebrand factor (vWF, green) are standard markers used to identify endothelial cells. As shown FIG. 9C, insulin activation of eNOS at Ser1177 is markedly blunted in endothelial cells (EC's) isolated from visceral compared to SC fat.

Figure 9C:
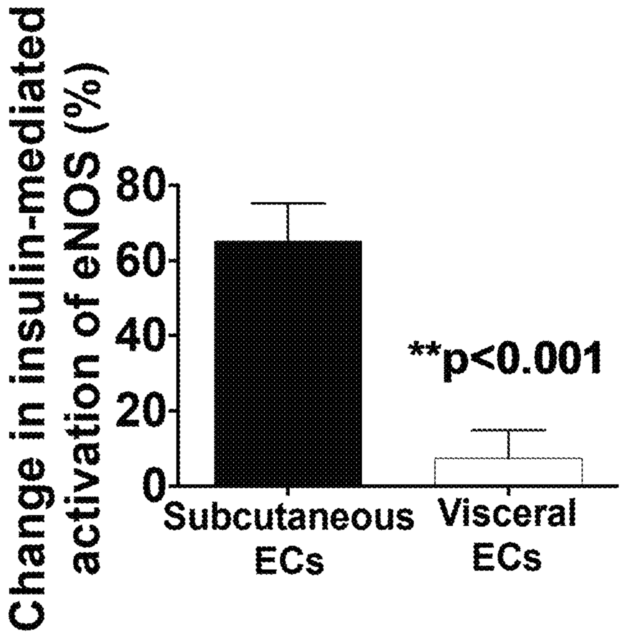

As shown in FIG. 9C, the data show that insulin activation of eNOS at Ser1177 is markedly blunted in endothelial cells (EC's) isolated from visceral compared to subcutaneous fat of obese subjects (**p<0.01, n=7, % change).

Role of Adipocyte-Specific FSP27 in Cross-Talk Between Adipocytes and Endothelial Cells.

FSP27 depletion in human primary adipocytes increases lipolysis and augmenting FFAs release in the media. In turn, elevated FFAs in obesity inhibits insulin-stimulated eNOS activation and promotes endothelial dysfunction.

Figure 10A:
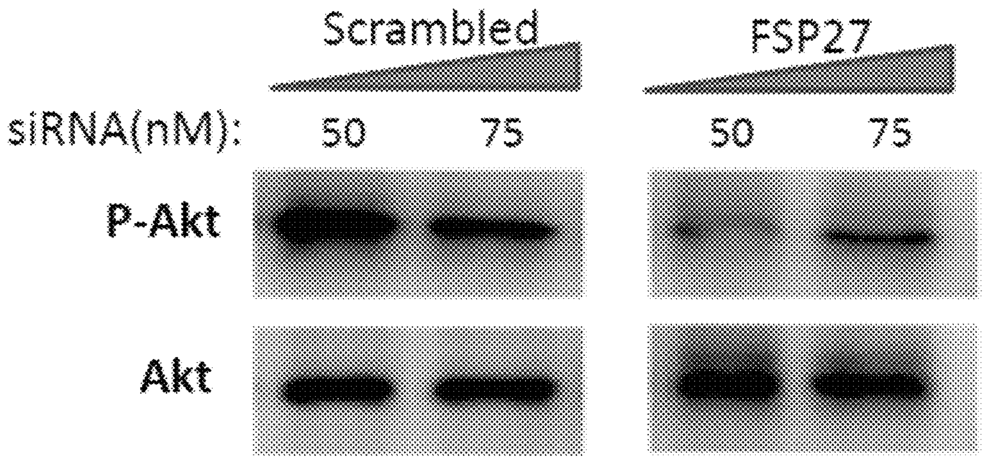
FIG. 10A: FSP27-KD adipocyte conditioned media added to HUVEC: The conditioned media was collected at 5th day after the knockdown from mature human subcutaneous white adipocyte.

FSP27-KD adipocyte conditioned media added to HUVEC: The conditioned media was collected at 5th day after the knockdown from mature human subcutaneous white adipocyte. This media was added to the HUVEC cells. Insulin-stimulated Akt phosphorylation was measured in HUVEC cells after 2 days of incubation with the conditioned media. FIG. 10A is a representative of three different sets of experiments performed with two different concentrations of FSP27 siRNA (50 nM, 75 nM).

Figure 10B:
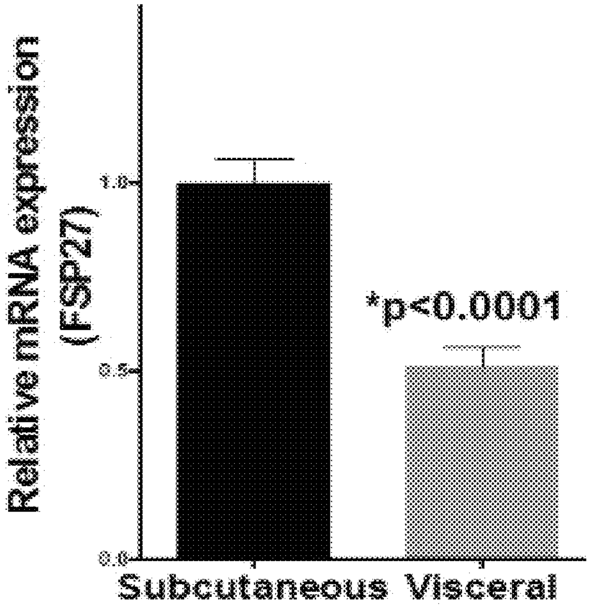
FIG. 10B-10C: Increased lipolysis in visceral fat is associated with decreased FSP27 expression: Basal FSP27 was significantly higher in subcutaneous vs. visceral fat depot by mRNA (FIG. 10B) and protein (FIG. 10C). Data are presented as ±SEM. (n=13, *p<0.0001 and p<0.001, respectively in paired samples).
Figure 10C:
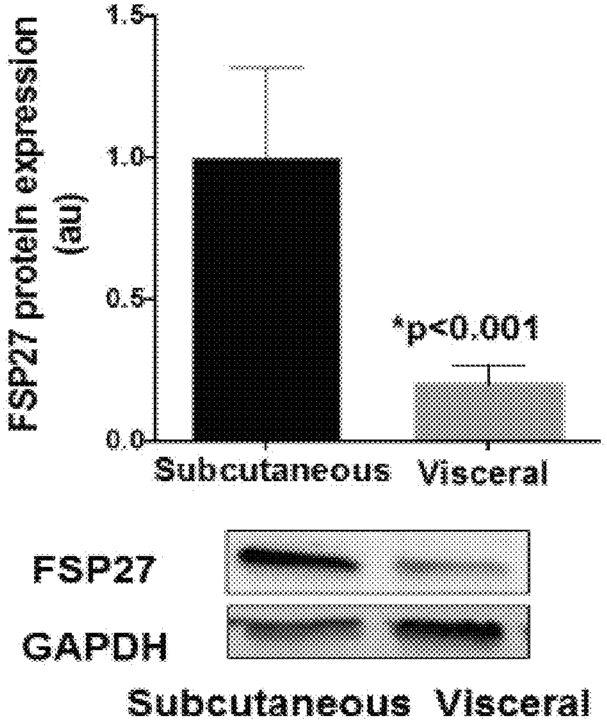

While not wishing to be bound by theory, it is now believed that lipolytic flux of FFAs regulated by FSP27 in adipocytes affect eNOS signaling and angiogenesis in endothelial cells in a paracrine manner, potentially through FFA. FIGS. 10B-10C show decreased FSP27 expression in the visceral adipose tissue of obese humans that is associated with increased lipolysis.

FSP27 Over-Expression Protects Against Vascular Dysfunction.

The role of FSP27 is examined in protection against obesity induced vascular dysfunction using adipose-specific and endothelial-specific human FSP27-overexpressing transgenic mice. Until now, the vascular pathophysiological importance of FSP27 and the associated signaling in these constructs have never been examined.

FSP27-KO Mice Showed Blunted Capillary Formation in Epididymal Adipose Tissue.

Figure 11A:
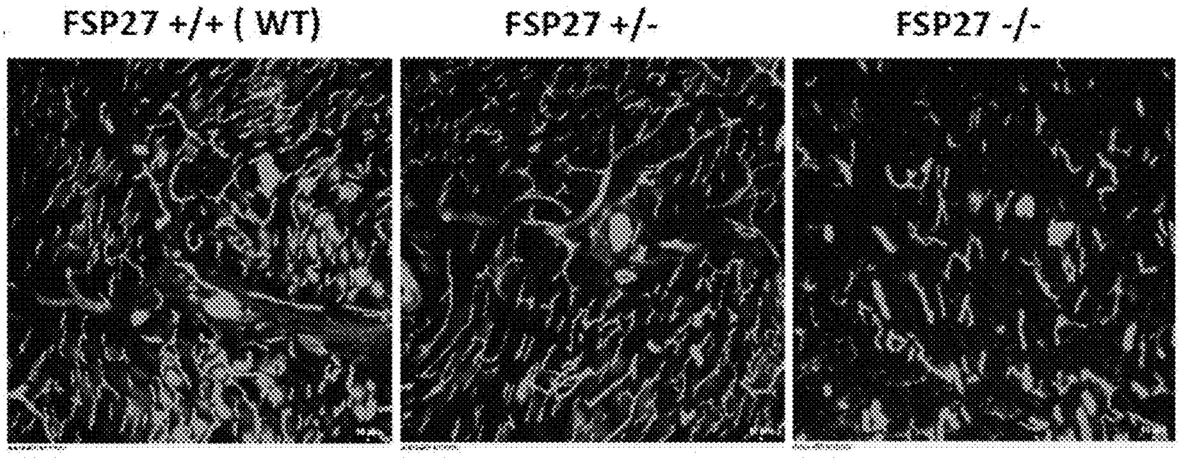
FIG. 11A: FSP27-KO mice show blunted capillary formation in adipose tissue. Histochemical staining of capillaries in subcutaneous adipose tissue of mice with isolectin B4.
Figure 11B:
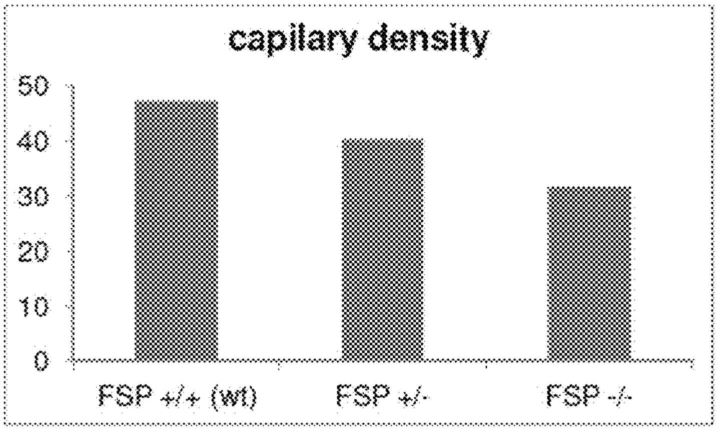
FIG. 11B: The data represents an average of capillary density in the subcutaneous adipose tissue of 2 mice per condition and demonstrate a "dose-dependent" loss of capillary network formation with FSP knock-down.

There is marked impairment in capillary formation (FIG. 11A and FIG. 11B), showing a role for FSP27 in regulating endothelial function and vascular proliferation. The capillary density was proportional to FSP27 expression, as heterozygous knockout mice ($FSP27^{+/-}$) showed an intermediate phenotype compared to the wild-types and full $FSP27^{-/-}$ mice. While not wishing to be bound by theory, it is now believed that adipose-specific FSP27 overexpression protects from HFD-induced lipolysis, insulin resistance and endothelial dysfunction. Mice over-expressing human FSP27 specifically in fat or endothelial cells are used to characterize the cell-autonomous function(s) of FSP27 in regulating insulin signaling, eNOS activation, angiogenesis, vasodilation, and metabolic phenotype.

Generation of Adipocyte-Specific as Well as Endothelial-Specific Human FSP27-Overexpressing Transgenic Mice.

Figure 12:
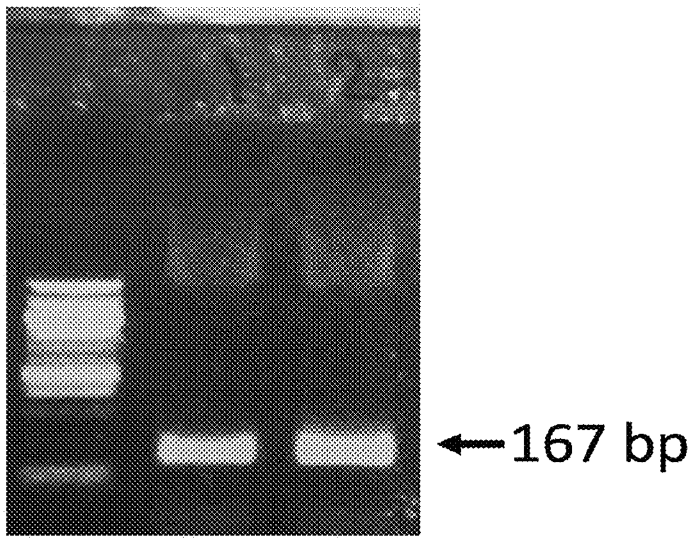
FIG. 12: Generation of ROSA26-FSP27 mice. The 167 bp, band, amplifying FSP27 exons 3 and 4, confirms successful targeting of FSP27 into the ROSA26 locus.

FSP27-overexpression is vasculo-protective. FSP27 has been cloned in ROSA26-CMV-loxSTOPlox vector and generated mice which conditionally over-express FSP27 (FIG. 12).

Figure 13A:
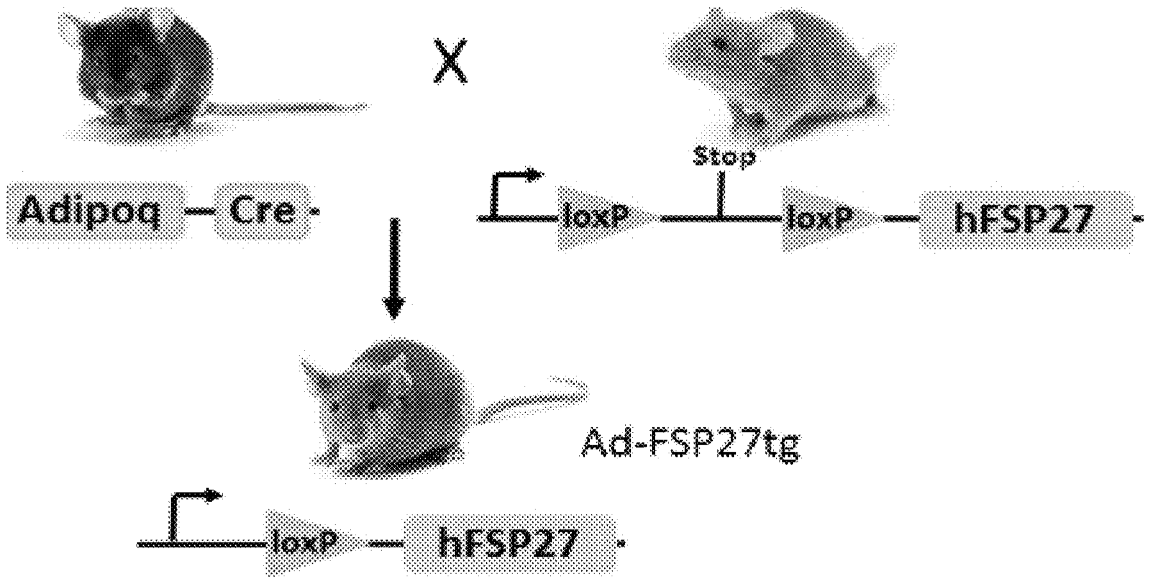
Figure 13B:
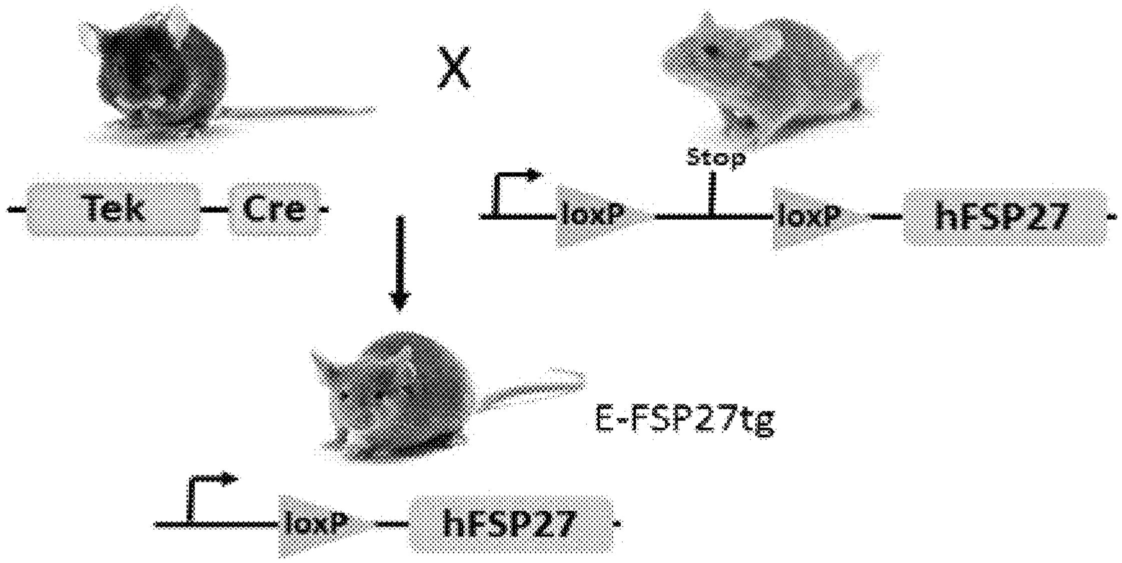
Figure 13C:
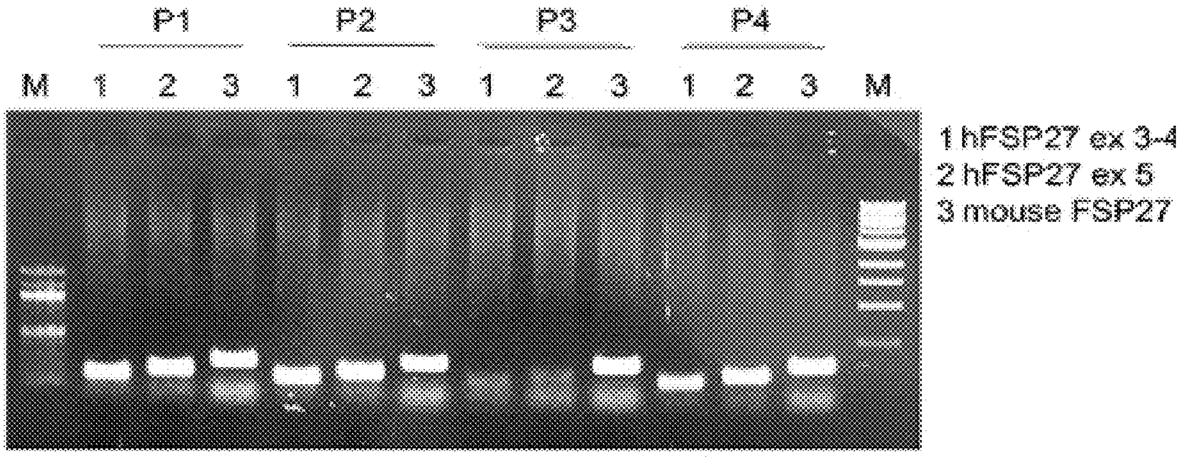

The mice were crossed with Adipoq-cre mice to specifically over-express FSP27 in adipose tissue, (Ad-FSP27tg). First generation Ad-FSP27tg mice are shown in (FIG. 13A). To generate endothelial-specific FSP27tg mice, the conditionally overexpressed FSP27 mice (FIG. 12) are crossed with B6.Cg-Tg(Tek-cre)1Ywa/J mice to specifically over-express FSP27 in endothelial cells (E-FSP27tg mice) (FIG. 138). FIG. 13C shows the genotyping results of F1 pups containing hFSP27 transgene (Ln 1 and 2).

Measurement of Vascular Parameters in Ad-FSP27tg and E-FSP27tg Mice.

Human data showed that arteriolar vasodilator and angiogenic function of the microvasculature in human adipose tissue was enhanced upon treatment with recombinant FSP27 (see FIG. 3, FIG. 6). Thus, again, while not wishing to be bound by theory, it is now believed that overexpression of FSP27 in adipose tissue and/or endothelial cells protects mice from high-fat diet induced endothelial dysfunction.

To confirm that these animal models show the cell-specific importance of FSP27 over-expression, and their respective vascular and metabolic phenotypes, the insulin responsiveness of adipose tissue is to be assessed by collecting tissues 10 minutes after intraperitoneal delivery of 0.75 U/kg of insulin. Akt and eNOS phosphorylation are to be evaluated by Western Blot and densitometric quantification of the pAkt(S473)/Akt and peNOS(S1179)/eNOS ratios. Also, phosphorylation of InsRβ, Akt1, ERK1/2, foxo1, and eNOS (by Western analysis) in aorta and femoral arteries is to be examined, since endothelial cells constitute approx. 50% of cellular populations in this tissue.

Further, endothelial cells will be isolated from the adipose tissues of test mice and WT mice by FACS sorting and analyzed for insulin-stimulated Akt phosphorylation and eNOS phosphorylation at baseline and in the presence of exogenous recombinant FSP27.

Endothelial function/dysfunction in mouse aortic rings harvested from the different experimental groups of mice (WT vs. transgenic mice under normal chow vs. high fat diet) are also to be evaluated. Insulin-stimulated vasodilation is to be assessed by standard methods that are similar to the studies performed on human vessels harvested from fat (see FIG. 3).

For comparison and further characterization, vessel contractile and relaxation responses to phenylephrine and insulin, respectively, are also assessed. Capillary density is to be examined by histochemical staining of adipose tissue capillaries using isolectin B4, and quantified as shown in FIG. 12. Angiogenic capacity is to be assessed using fat-pad sprouting assays and tube formation as depicted in FIG. 6.

Figure 14:
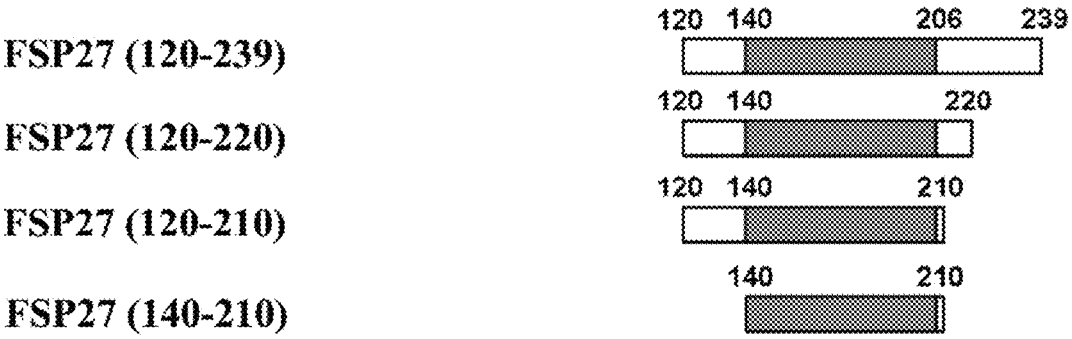
FIG. 14: Schematic illustration of FSP27 fragments/mutants: FSP27 (120-239); FSP27 (120-220); FSP27 (120-210); and, FSP27 (140-210).

FIG. 14 is a schematic illustration of FSP27 fragments/mutants: FSP27 (120-239); FSP27 (120-220); FSP27 (120-210); and, FSP27 (140-210).

Figure 15:
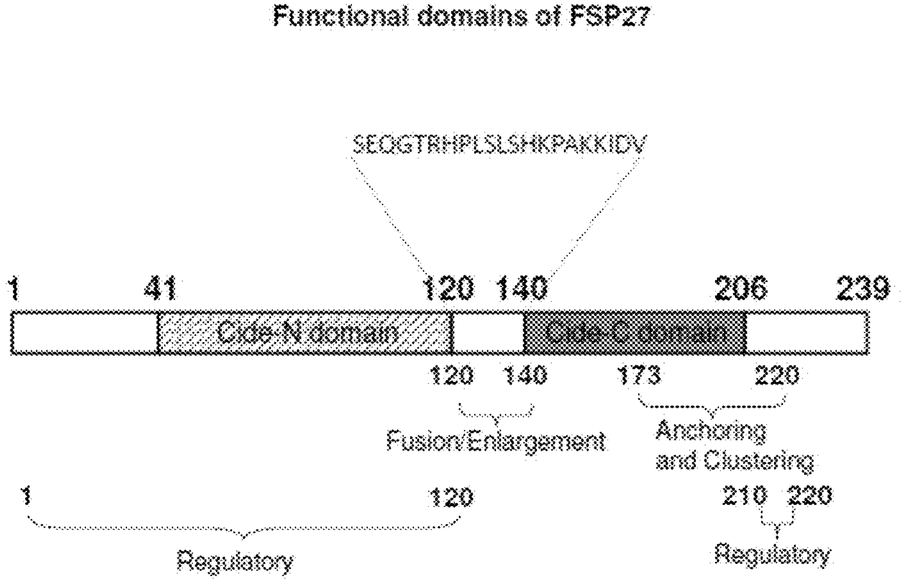
FIG. 15: Schematic illustration of full length FSP27 showing domains associated with lipid droplet dynamics, showing CF4, SEQ ID NO: 4.

FIG. 15 is a schematic illustration of full length FSP27 showing domains associated with lipid droplet dynamics, and the segment that has shown maximum efficacy towards cardiovascular disease effect in cells.

FIG. 16: FSP27 sequence is conserved in vertebrates; for example, >90% conserved sequence in FSP27 in: humans (SEQ ID NO: 12); mouse (SEQ ID NO: 13); monkey (SEQ ID NO: 14); dog (SEQ ID NO: 15); cow (SEQ ID NO: 16); and, frog (SEQ ID NO: 17).

FIG. 17: Table 1, showing the amino acid sequence detail of the relevant peptides, listing SEQ ID NOs: 1-12.

Adipocyte-Specific Lipid-Droplet Associated Protein, FSP27, is Also Expressed in Endothelial Cells.

Figure 18A:
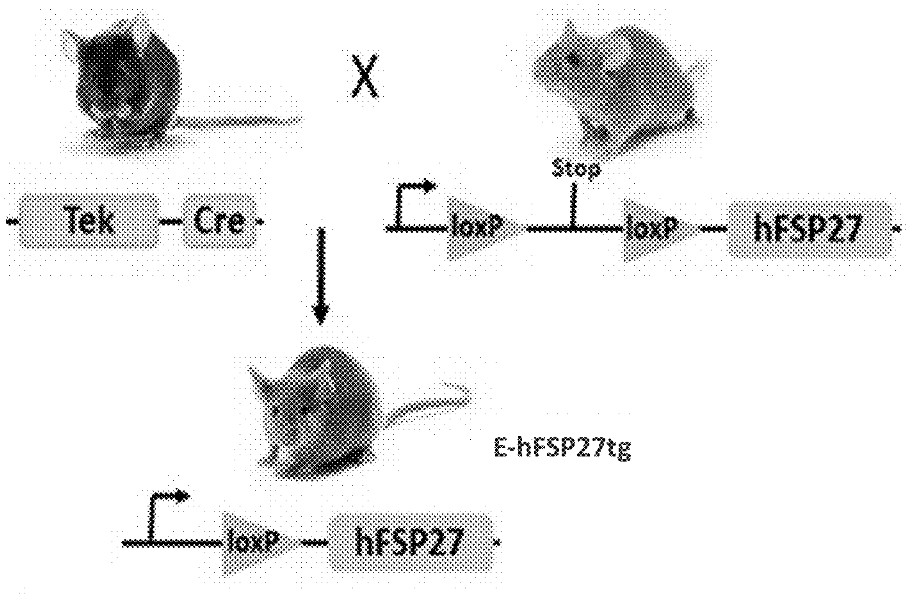
FIGS. 18A-18B: Mice expressing human-FSP27 transgene specifically in their endothelial cells (E-hFSP27tg) were generating by crossing hFSP27-floxed mice with Tek-cre mice
Figure 18B:
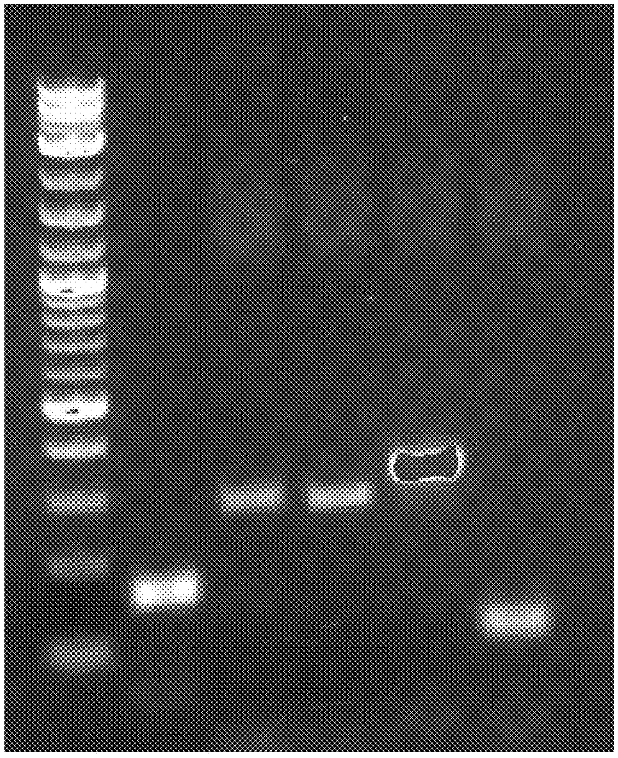
Figure 19:
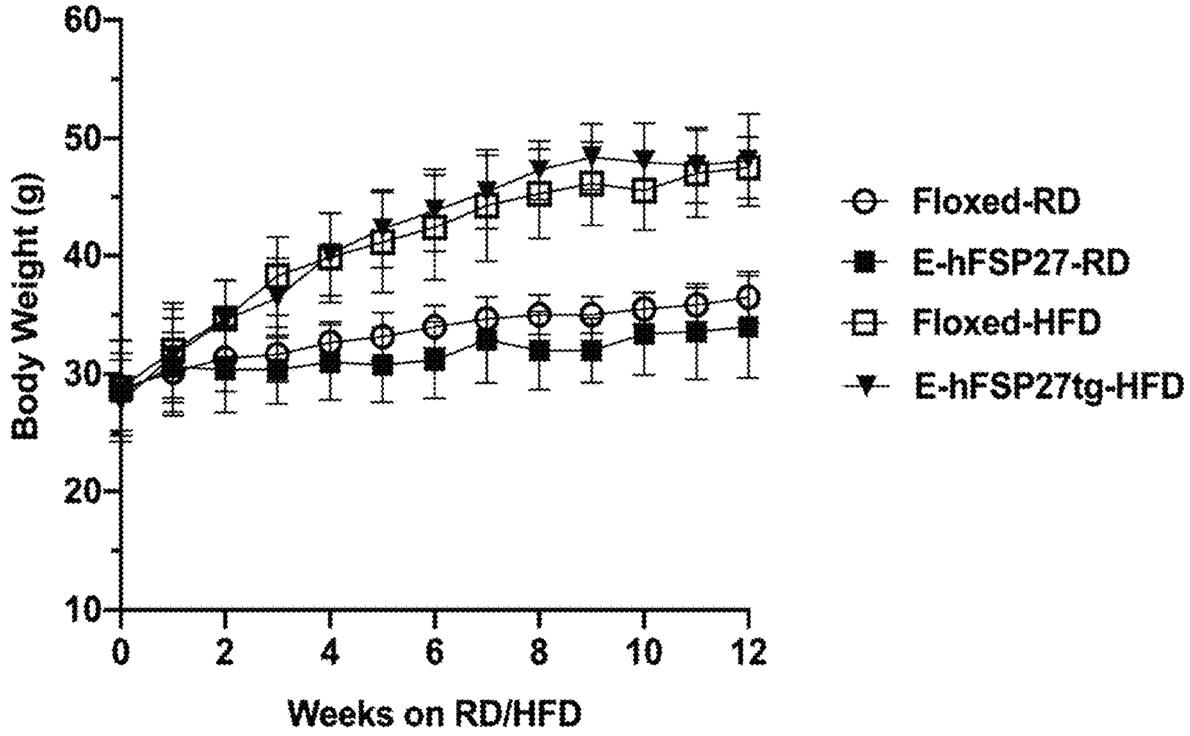
FIG. 19: Body weight gain in a cohort of floxed and E-hFSP27tg mice on regular diet and high-fat diet.

A mouse model was generated that expresses a single allele of FSP27 transgene specifically in the endothelial cells (E-hFSP27tg) (See FIGS. 18A-18B). On regular chow and high-fat diets, these mice gain weight similar to the control mice (floxed-wild type) (See FIG. 19).

Figure 20A:
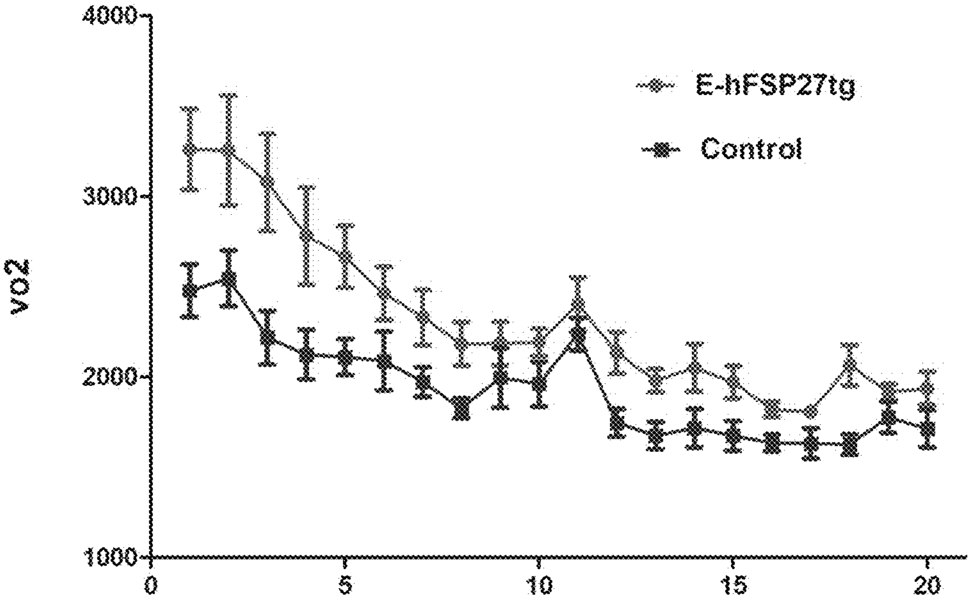
Figure 20B:
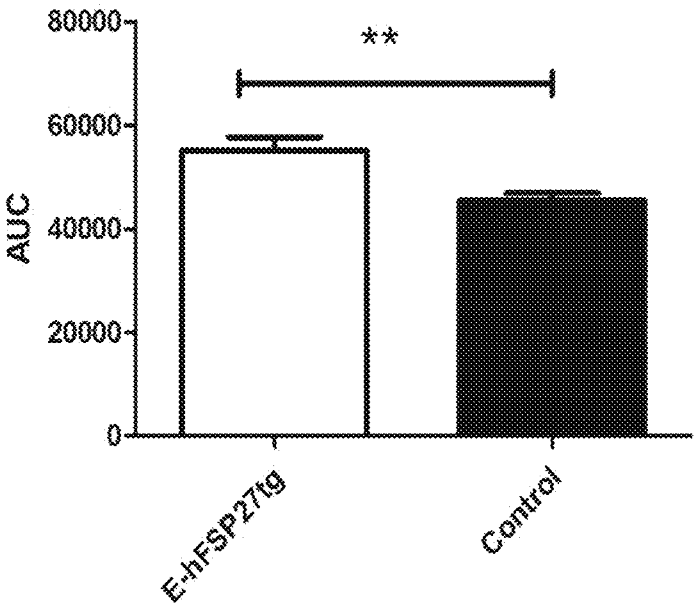
Figure 21A:
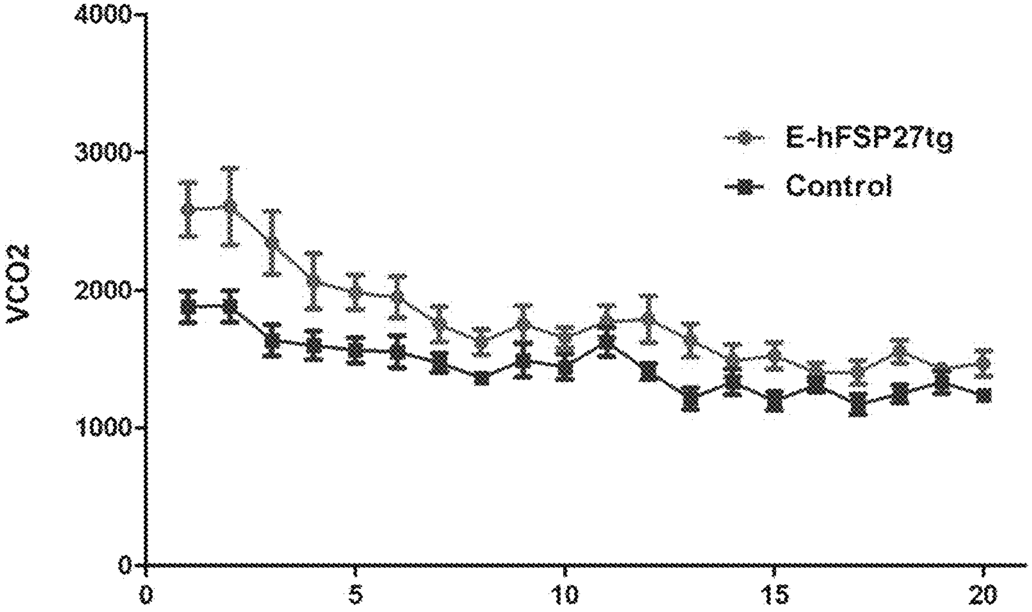
FIG. 21A-21B: Increased oxygen consumption ($CO_2$ release) in E-hFSP27tg mice compared to FSP27-floxed (Control) mice. At the age of 4 months these mice were fed 60% high-fat diet for 2 months.
Figure 21B:
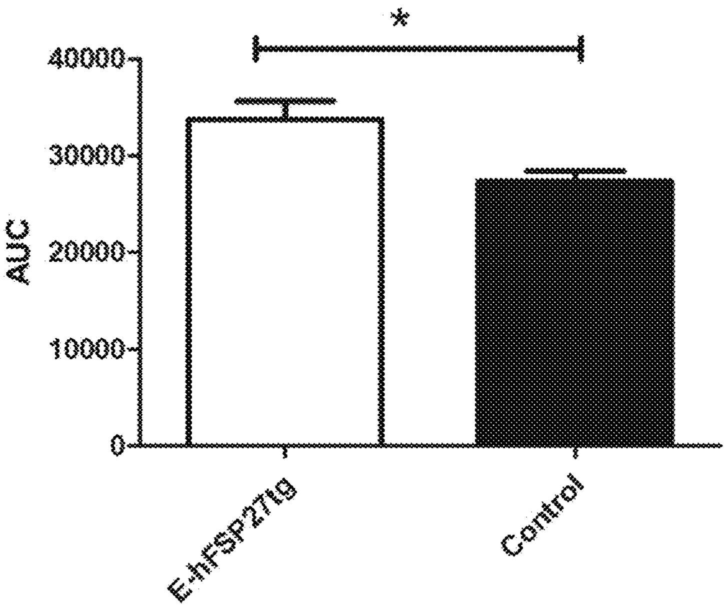
Figure 22A:
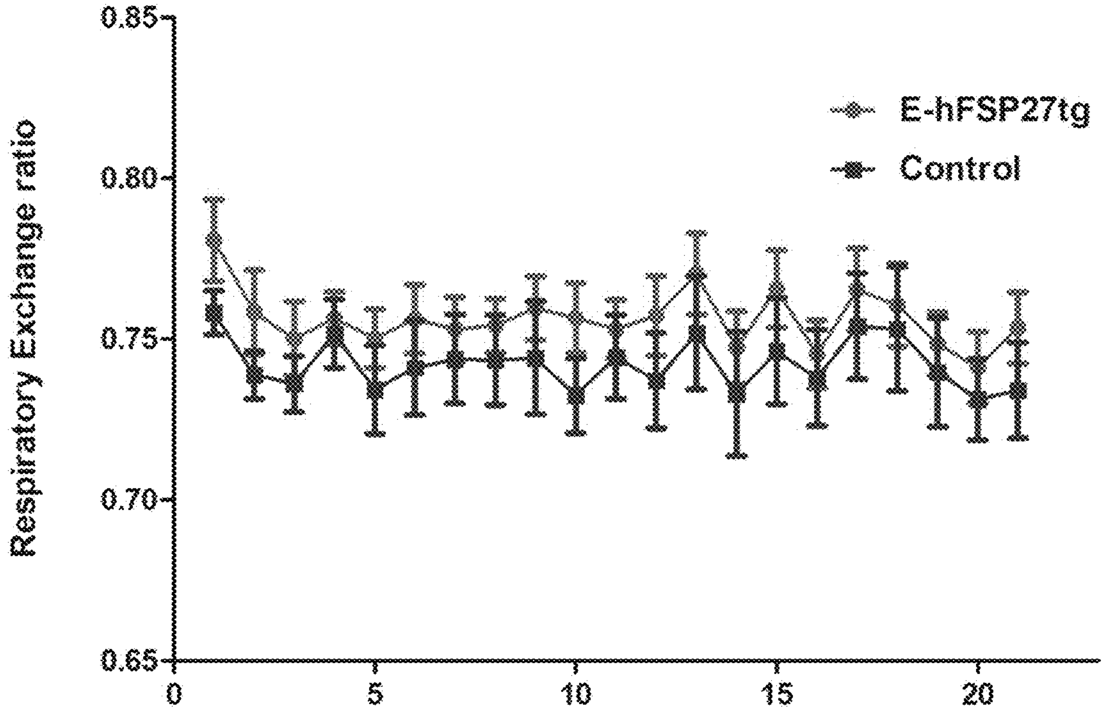
FIG. 22-22R: Respiratory exchange ratio (RER) in E-hFSP27tg mice compared to FSP27-floxed (Control) mice. At the age of 4 months these mice were fed 60% high-fat diet for 2 months.
Figure 22B:
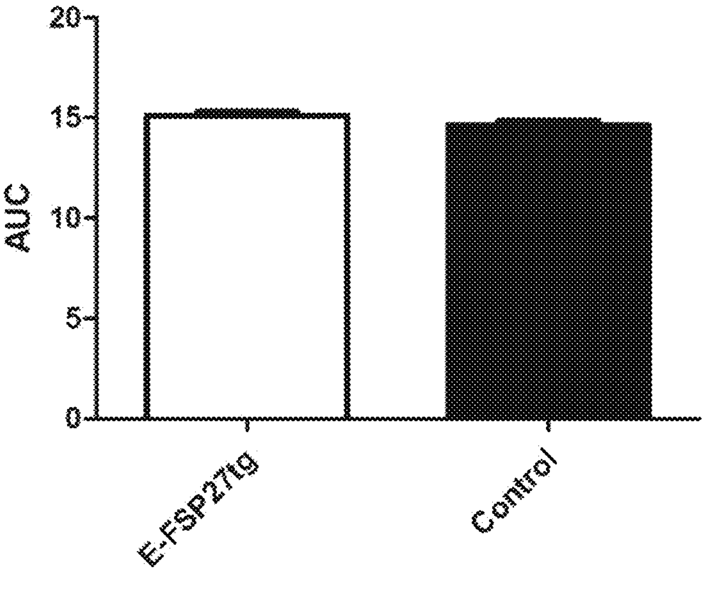

Even after feeding high-fat diet, their metabolic profile, like $VO_2$, $VCO_2$, and RER is better compared to the control mice. FIGS. 20, 21, 22 show that the model mice have higher fatty acid oxidation in the muscle.

Figure 23:
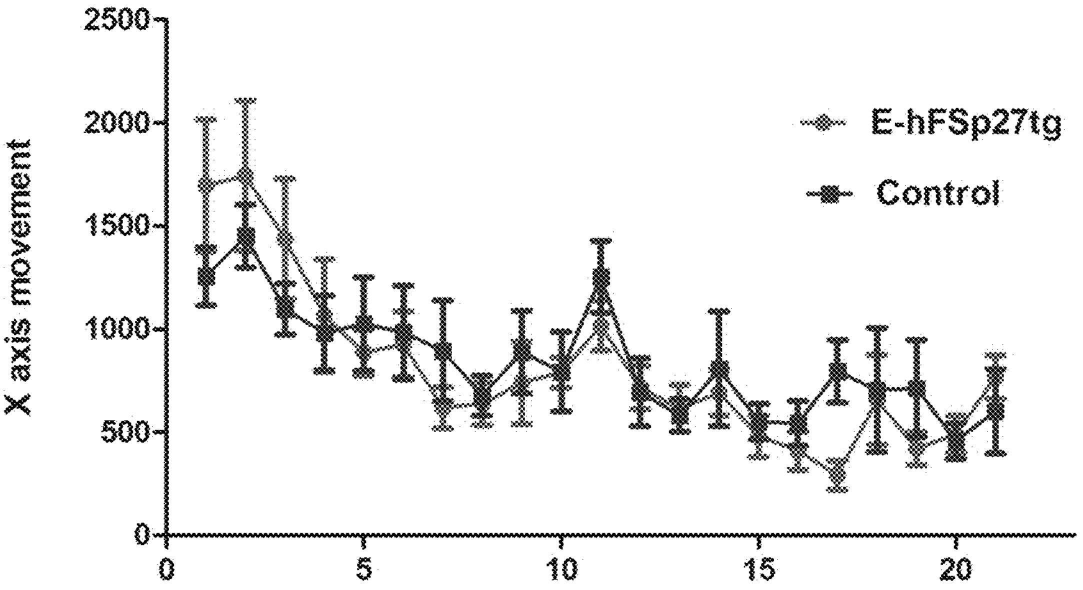
FIG. 23: Movement (activity) along X axis of E-hFSP27tg mice compared to FSP27-floxed (Control) mice. At the age of 4 months these mice were fed 60% high-fat diet for 2 months.
Figure 24:
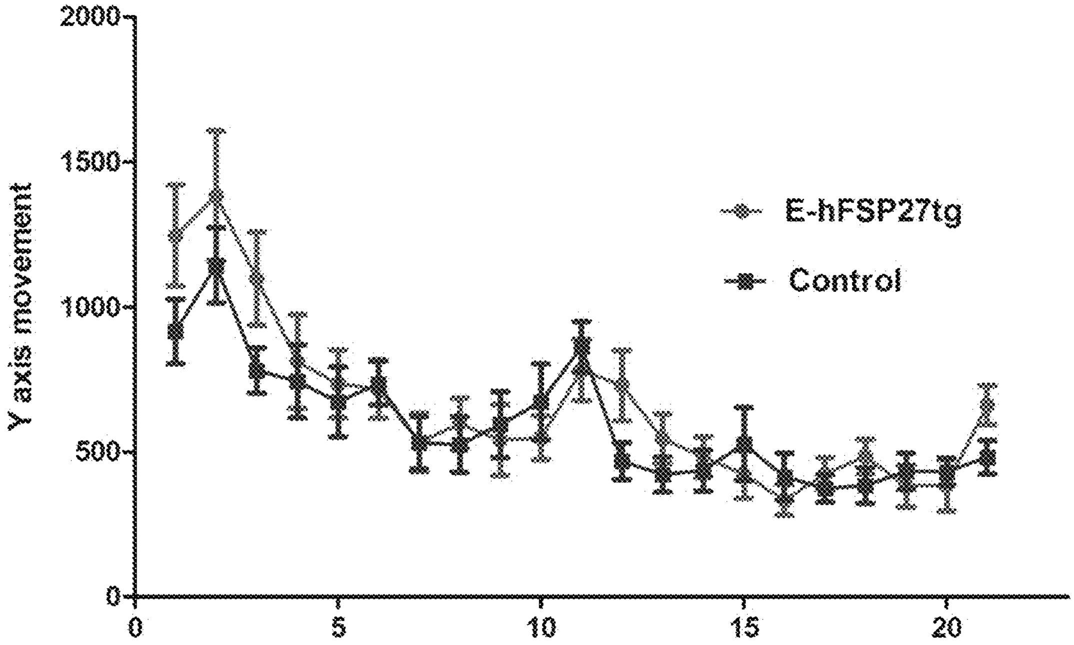
FIG. 24: Movement (activity) along Y axis of E-hFSP27tg mice compared to FSP27-floxed (Control) mice. At the age of 4 months these mice were fed 60% high-fat diet for 2 months.
Figure 25:
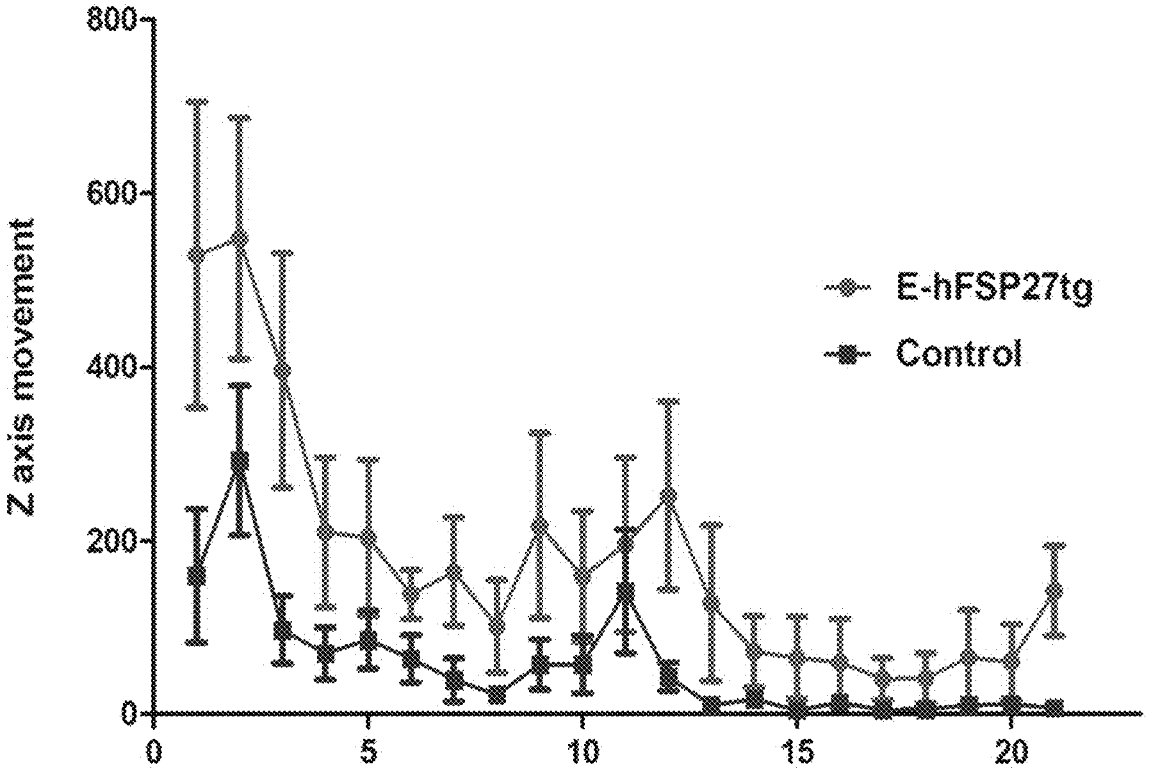
FIG. 25: Movement (activity) along Z-axis of E-hFSP27tg mice compared to FSP27-floxed (Control) mice. E-hFSP27tg mice had more activity/movement along the Z-axis. At the age of 4 months these mice were fed 60% high-fat diet for 2 months.

The model mice also show higher activity (FIGS. 23, 24, 25).

Figure 26:
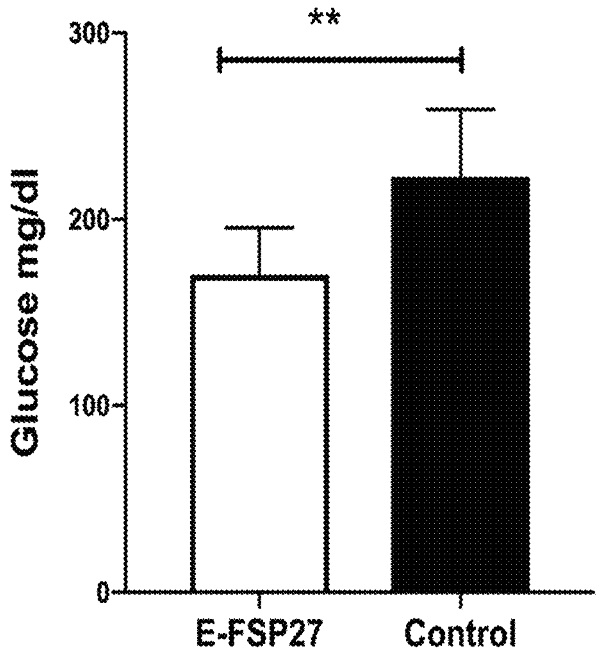
FIG. 26: Fasting glucose levels were increased E-hFSP27tg mice compared to FSP27-floxed (Control) mice. At the age of 4 months these mice were fed 60% high-fat diet (HFD) or regular-chow (RD) diet for 2 months.
Figure 27:
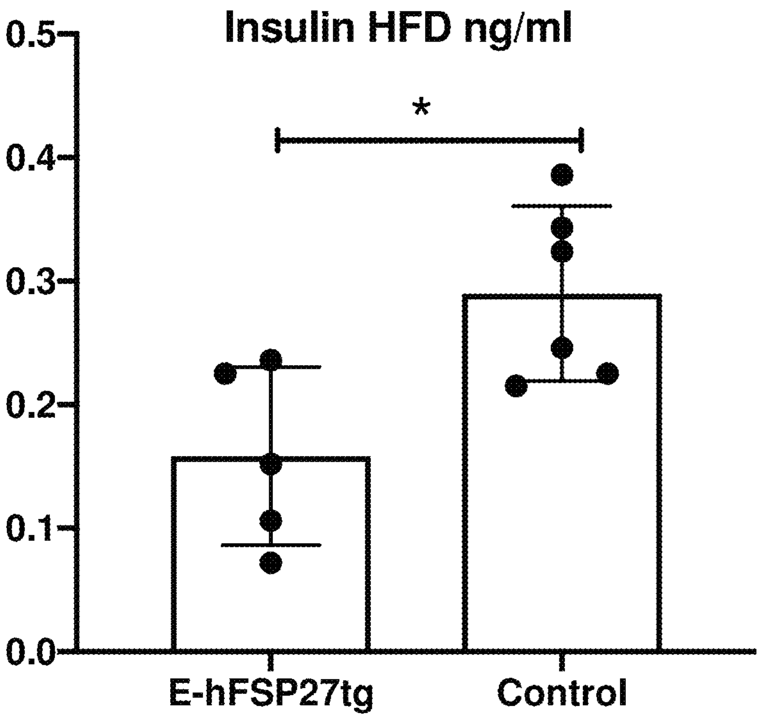
FIG. 27: Fasting insulin levels were decreased E-hFSP27tg mice compared to FSP27-floxed (Control) mice. At the age of 4 months these mice were fed 60% high-fat diet (HFD) for 2 months.
Figure 28A:
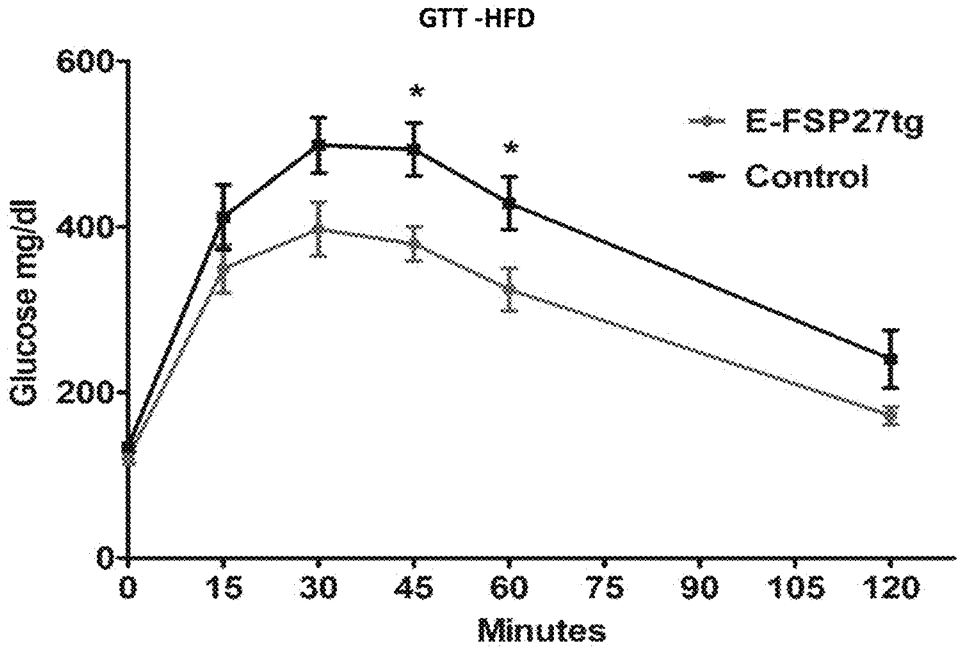
FIG. 28A-28: Glucose tolerance was significantly increased in E-hFSP27tg mice compared to FSP27-floxed (Control) mice. At the age of 4 months these mice were fed 60% high-fat diet (HFD) or regular-chow (RD) diet for 2 months.
Figure 28B:
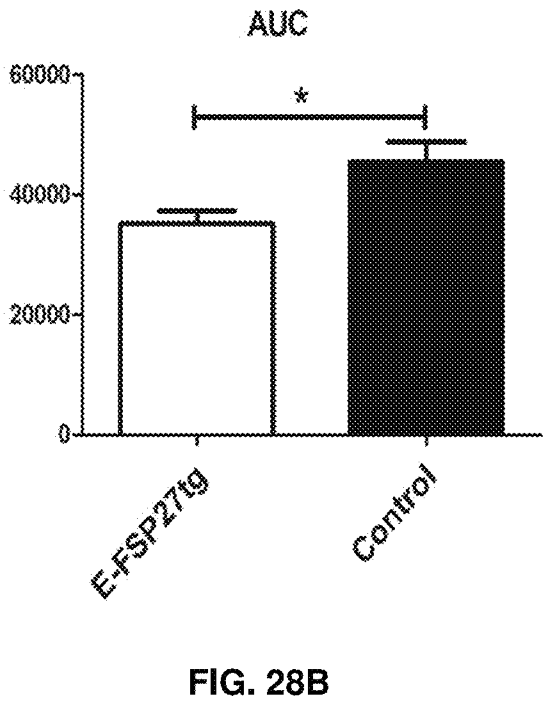
Figure 28C:
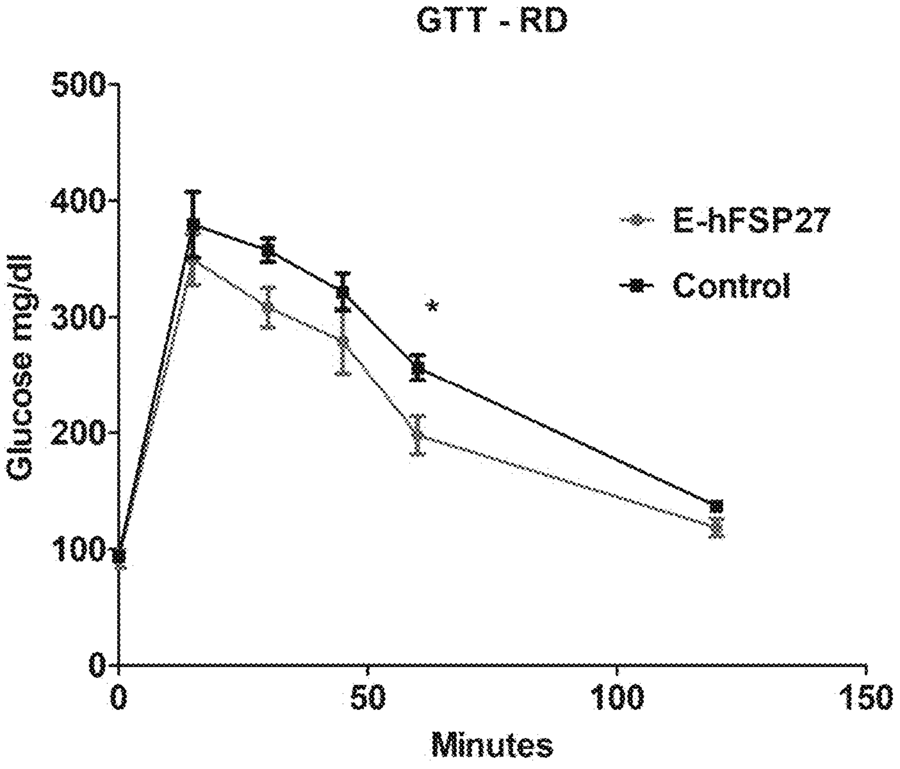
Figure 28D:
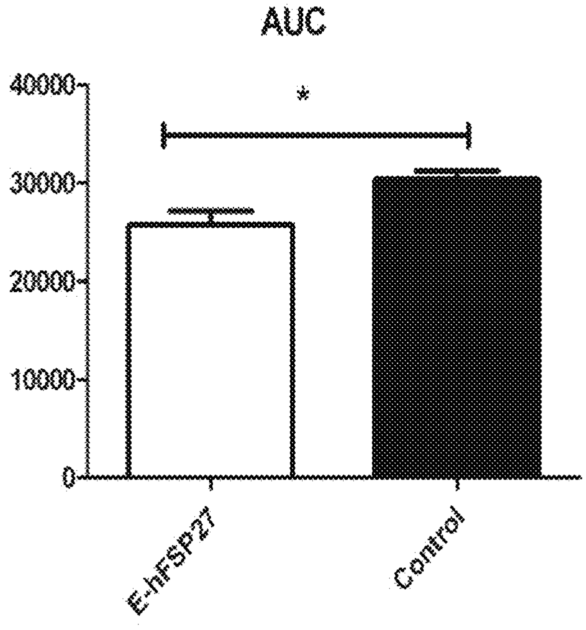
Figure 29A:
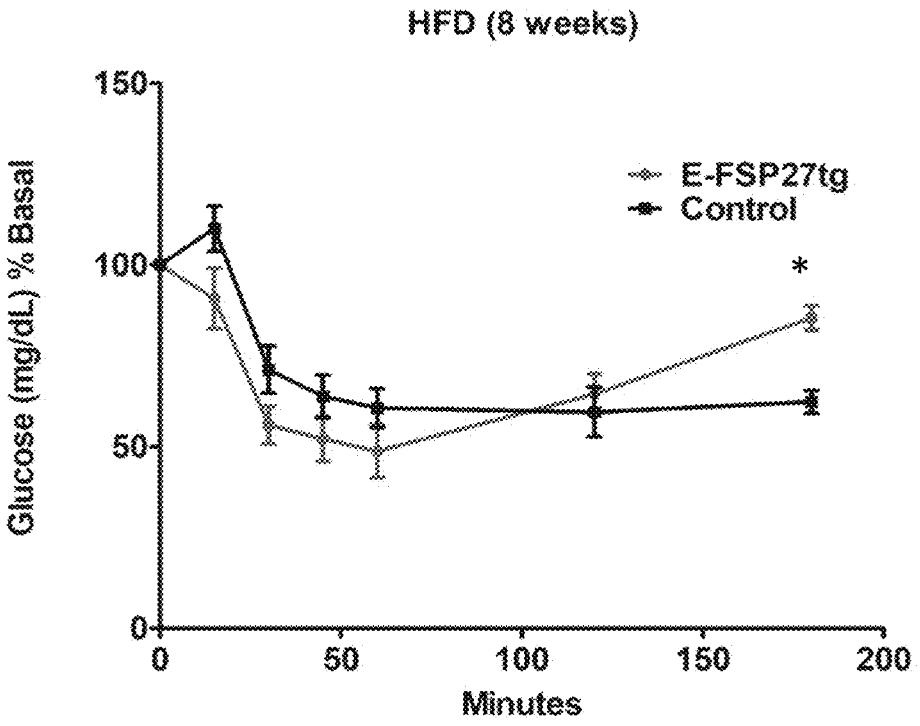
FIG. 29A-29D: Insulin tolerance (insulin sensitivity) was significantly increased in E-hFSP27tg mice compared to FSP27-floxed (Control) mice. At the age of 4 months these mice were fed 60% high-fat diet (HFD) or regular-chow (RD) diet for 2 months.
Figure 29B:
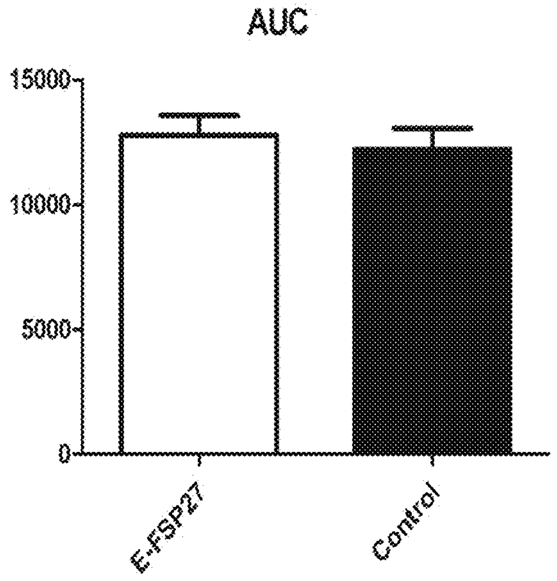
Figure 29C:
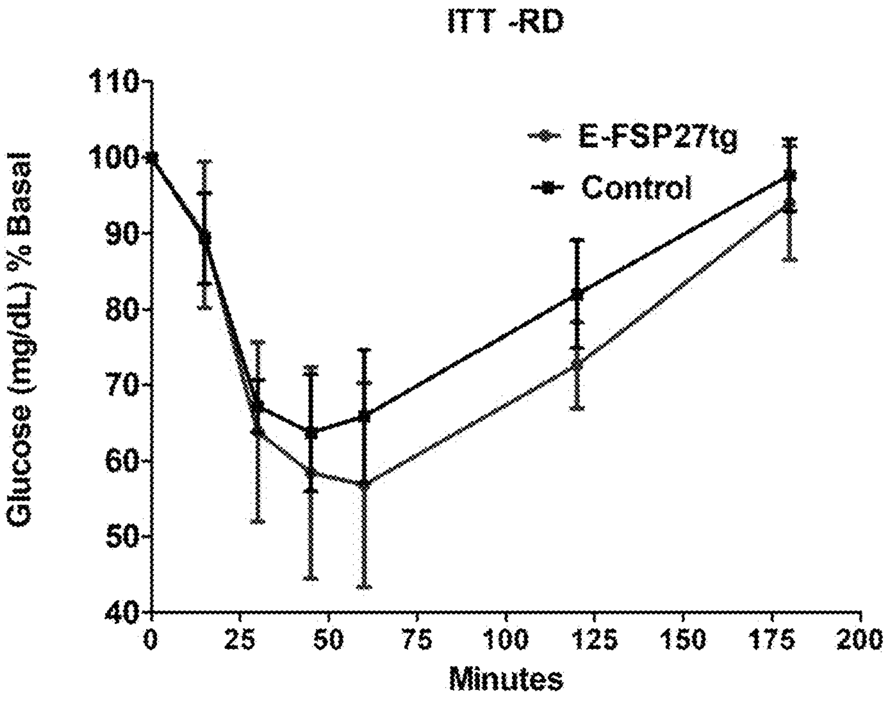
Figure 29D:
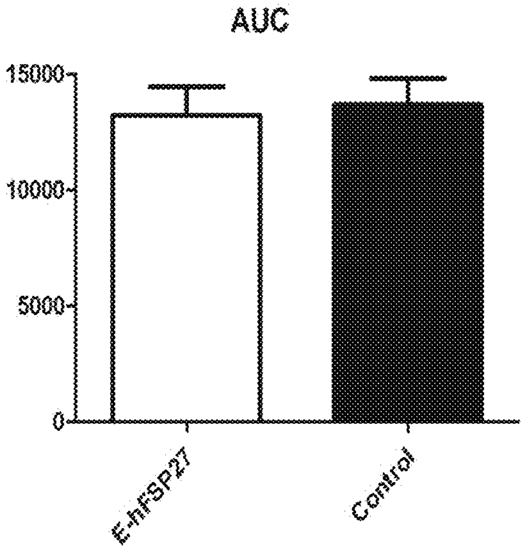

Both regular-chow and high-fat-fed E-hFSP27 mice have lower fasting blood glucose compared to the controls (FIG. 26), and E-hFSP27tg mice showed lower fasting insulin levels showing that they are protected against hyperinsulinemia (FIG. 27).

The model mice are protected against high-fat diet induced insulin resistance as shown by glucose tests (FIG. 28) insulin tolerance tests (FIG. 29).

Figure 30A:
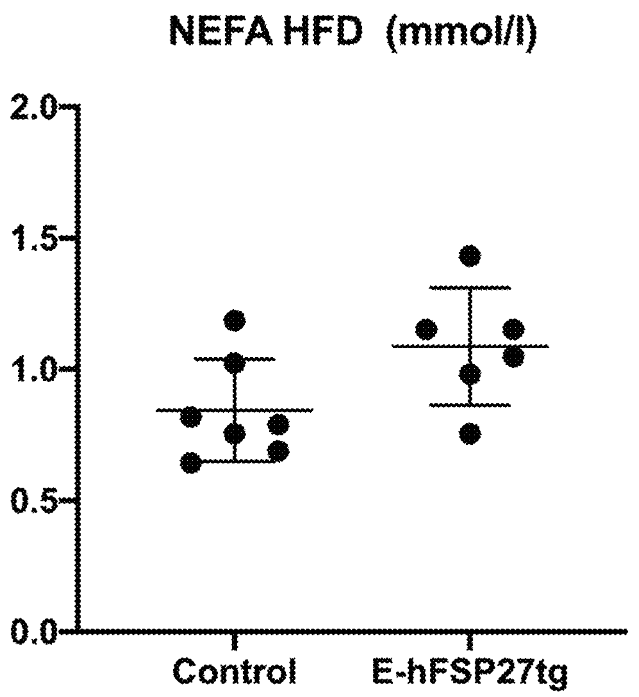
FIG. 30A-30B: Serum Free fatty acid levels in E-hFSP27tg mice compared to FSP27-floxed (Control) mice. At the age of 4 months these mice were fed 60% high-fat diet (HFD) or regular-chow (RD) diet for 2 months. No significant change in serum free fatty acid levels was observed.
Figure 30B:
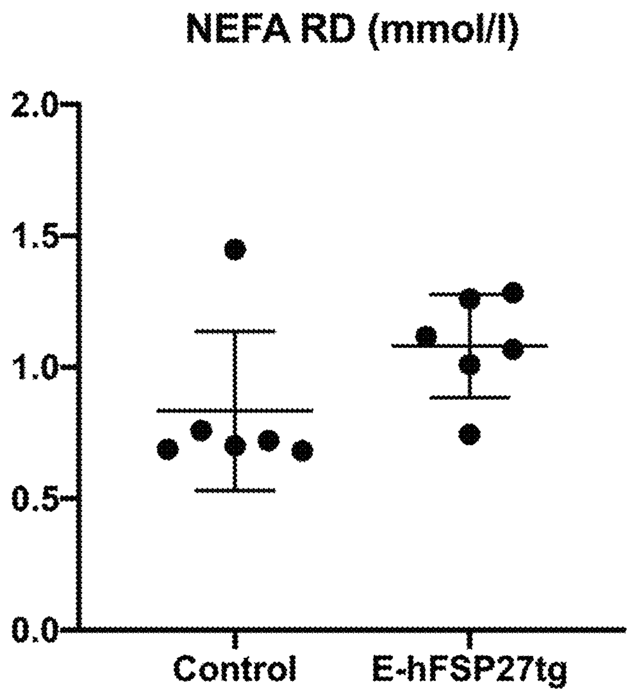
Figure 31A:
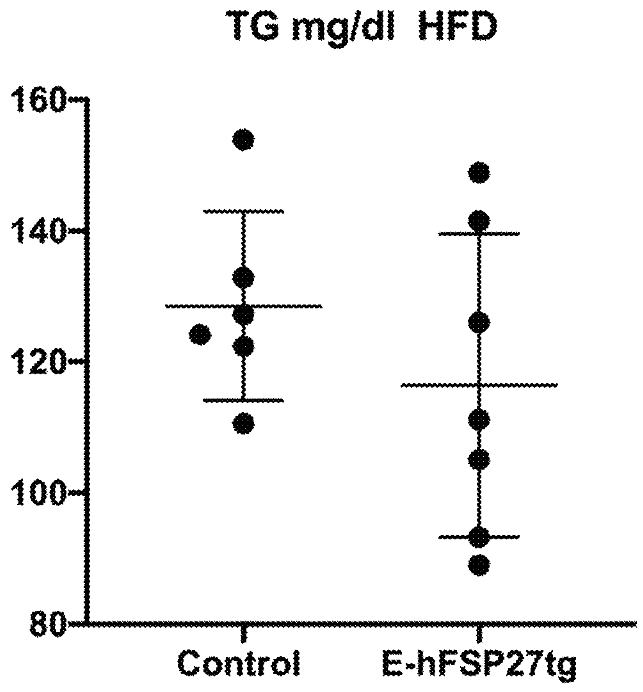
FIGS. 31A-31B: Serum triglyceride levels in E-hFSP27tg mice compared to FSP27-floxed (Control) mice. At the age of 4 months these mice were fed 60% high-fat diet (HFD) or regular-chow (RD) diet for 2 months. No significant change in serum triglyceride levels was observed.
Figure 31B:
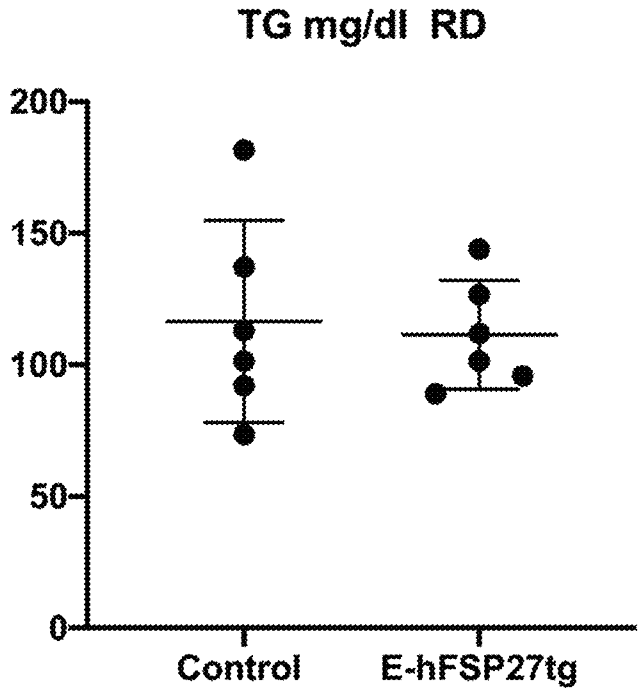
Figure 32A:
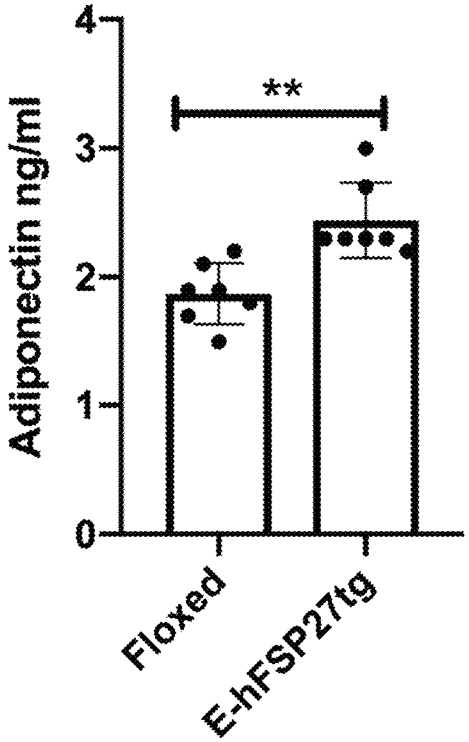
FIGS. 32A-32B: Serum adiponectin levels in E-hFSP27tg mice was significantly increased compared to FSP27-floxed (Control) mice. At the age of 4 months these mice were fed 60% high-fat diet (HFD) where as there was no significant change in adiponectin in regular died fed mice.
Figure 32B:
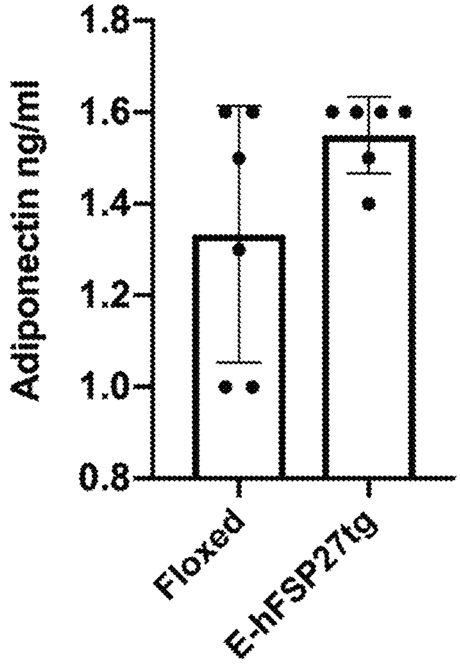
Figure 33:
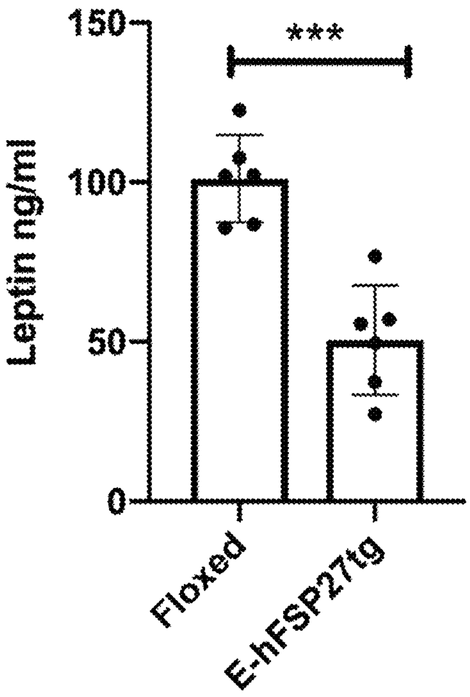
FIG. 33: Serum leptin levels were decreased in E-hFSP27tg mice compared to FSP27-floxed (Control) mice. At the age of 4 months these mice were fed 60% high-fat diet (HFD) for 2 months.

The circulatory fatty acids and triglycerides are normal (FIGS. 30-31). Serum adiponectin levels in E-hFSP27tg mice were higher (FIG. 32) whereas leptin levels were lower (FIG. 33) than the control mice.

Figure 34A:
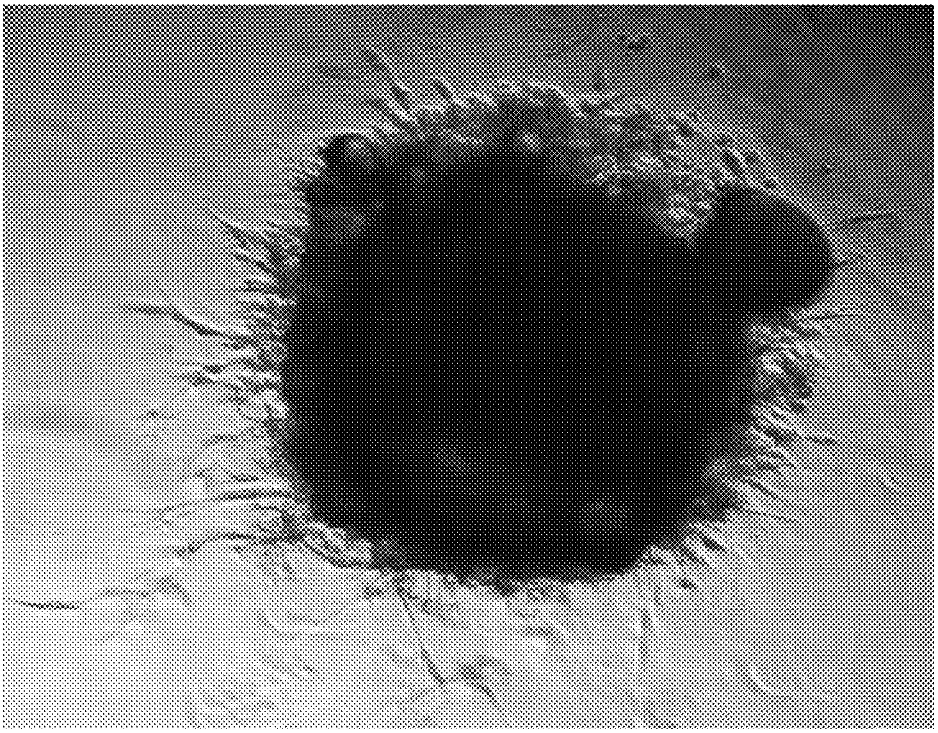
FIGS. 34A-34B: In an in-vitro assay adipose tissue E-hFSP27tg mice showed higher sprouting indicating increased angiogenesis in E-hFSP27tg compared to the FSP27-floxed (Control) mice.
Figure 34B:
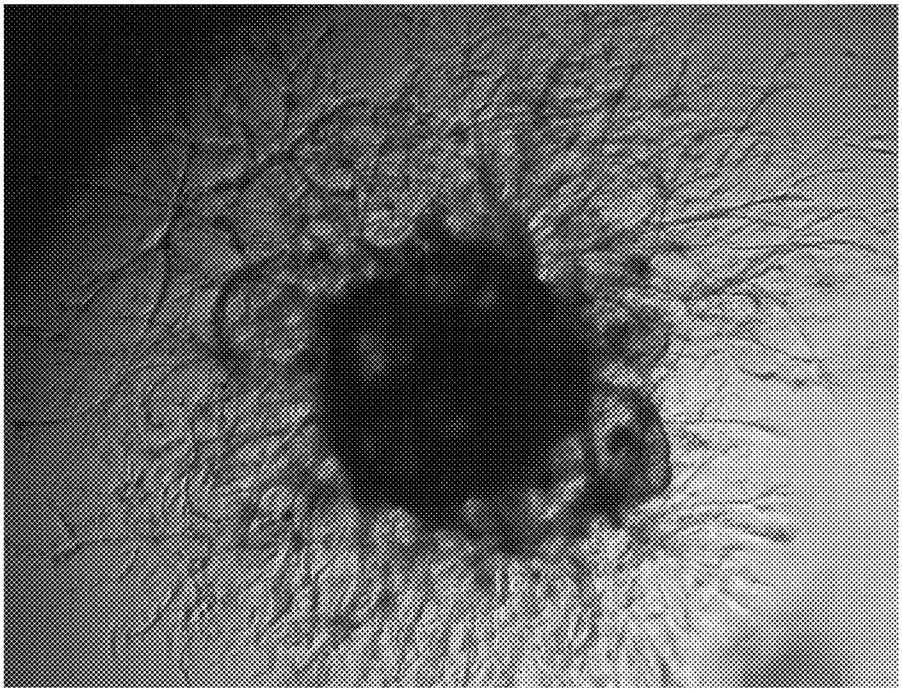
Figure 35:
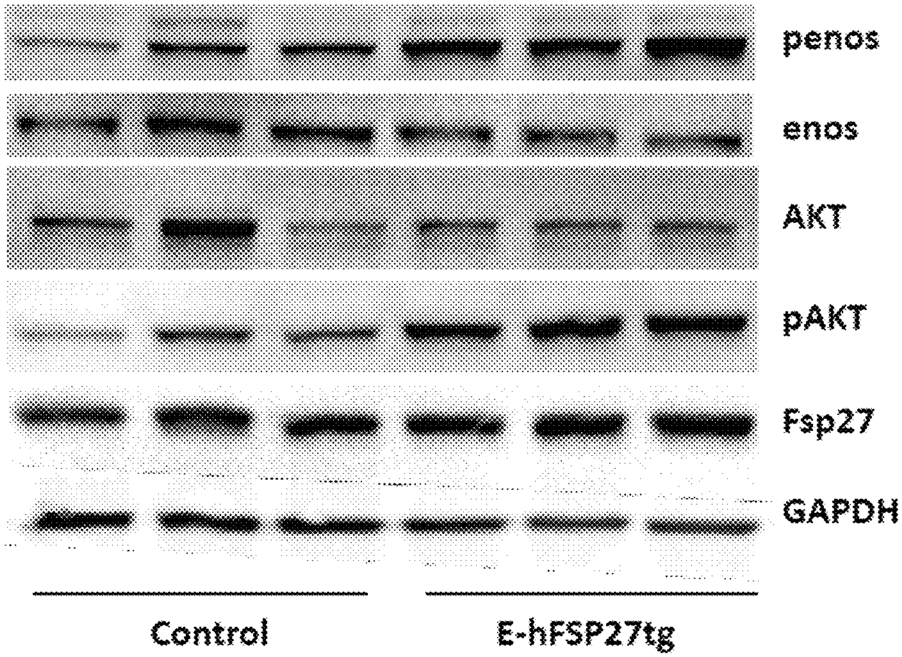
FIG. 35: Western blot representing the expression of levels enos, penos, AKT, pAKT, FSP27 and GAPDH in gonadal white adipose tissue of E-hFSP27tg mice and FSP27-floxed (Control) mice. At the age of 4 months these mice were fed 60% high-fat diet (HFD) for 2 months. Results show that AKT phosphorylation (insulin signaling) and eNOS phosphorylation (endothelial function) is improved in E-hFSP27tg mice.

Angiogenesis, insulin sensitivity, and eNOS activation in the adipose tissue of control vs transgenic mice were examined to determine the mechanism of action. eNOS activation is associated with angiogenesis and vasodilation of blood vessels, which is protective against cardiovascular disease. The results showed higher capillary sprouting (FIGS. 34A-34B) in adipose tissue of E-hFSP27tg mice associated with higher insulin-stimulated AKT and eNOS phosphorylation (FIG. 35).

Overall, the results show that the transgenic mice expression human-FSP27 in endothelial cells are protected against insulin resistance and show higher systemic metabolic health.

Other Examples

Pharmaceutical Compositions

A pharmaceutical composition as described herein may be formulated with any pharmaceutically acceptable excipients, diluents, or carriers. A composition disclosed herein may comprise different types of carriers depending on whether it is to be administered in solid, liquid, or aerosol form, and whether it needs to be sterile for such routes of administration as injection. Compositions disclosed herein can be administered in a suitable manner, including, but not limited to topically (i.e., transdermal), subcutaneously, by localized perfusion bathing target cells directly, via a lavage, in creams, in lipid compositions (e.g., liposomes), formulated as elixirs or solutions for convenient topical administration, formulated as sustained release dosage forms, or by other method or any combination of the forgoing as would be known to one of ordinary skill in the art (see, for example, Remington's Pharmaceutical Sciences, 2003, incorporated herein by reference).

The compositions provided herein are useful for treating animals, such as humans. A method of treating a human patient according to the present disclosure includes the administration of a composition, as described herein.

The phrases "pharmaceutical" or "pharmacologically acceptable" refer to molecular entities and compositions that produce no adverse, allergic, or other untoward reaction when administered to an animal, such as, for example, a human. A carrier or diluent may be a solid, semi-solid, or liquid material which serves as a vehicle, excipient, or medium for the active therapeutic substance. Some examples of the diluents or carriers which may be employed in the pharmaceutical compositions of the present disclosure are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of *theobroma, arachis* oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol, and propellants such as trichloromonofluoromethane, dichlorodifluoromethane, and dichlorotetrafluoroethane.

The phrase "chemotherapeutic agent" refers to a therapeutic agent known to be used in treating a subject that has been diagnosed with cardiovascular disease. Some examples of general classes of chemotherapeutic agents of the present disclosure include akylating agents, anthracyclines, cytoskeletal disruptors, epothilones, histone deacetylase inhibitors, inhibitors of topoisomerase I and II, kinase inhibitors, nucleotide analogs and precursor analogs, peptide antibiotics, platinum-based agents, retinoids, and vina akaloids and derivatives. Of these general classes, specific examples include but are not limite to doxorubicin (Adriamycin), sorafenib tosylate, cisplatin, paclitaxel, gemcitabine, vemurafenib, dabrafenib, linsitinib, crizotinib, and cabozantinib.

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof, and in oils. Under ordinary conditions of storage and use, these preparations contain a preservative to prevent the growth of microorganisms. The pharmaceutical forms suitable for use include sterile aqueous solutions or dispersions and sterile powders for the extemporaneous preparation of sterile solutions or dispersions. In certain cases, the form should be sterile and should be fluid to the extent that easy injectability exists. It should be stable under the conditions of manufacture and storage and may optionally be preserved against the contaminating action of microorganisms, such as bacteria and fungi. The carrier can be a solvent or dispersion medium containing, for example, water, ethanol, a polyol (i.e., glycerol, propylene glycol, and liquid polyethylene glycol, and the like), suitable mixtures thereof, and/or vegetable oils. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, such as, but not limited to, sugars or sodium chloride.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, akyl methyl sulfoxides, pyrrolidones and luarocapram. Possible bases for compositions for topical application include polyethylene glycol, lanolin, cold cream, and petrolatum as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed time-period.

It is further envisioned the compositions disclosed herein may be delivered via an aerosol. The term aerosol refers to a colloidal system of finely divided solid or liquid particles dispersed in a liquefied or pressurized gas propellant. The typical aerosol comprises a suspension of active ingredients in liquid propellant or a mixture of liquid propellant and a suitable solvent. Suitable propellants include hydrocarbons and hydrocarbon ethers. Suitable containers can vary according to the pressure requirements of the propellant. Administration of the aerosol can vary according to subject's age, weight, and the severity and response of the symptoms.

Dosage

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and the route of administration. Depending upon the dosage and the route of administration, the number of administrations of a preferred dosage and/or an effective amount may vary according to the response of the subject. The compounds of the present disclosure are generally effective over a wide dosage range. The practitioner responsible for administration can, in any event, determine the concentration of active ingredient(s) in a composition and appropriate dose(s) for the individual subject.

Naturally, the amount of active compound(s) in each therapeutically useful composition may be prepared in such a way that a suitable dosage can be obtained in any given unit dose of the compound. Factors such as solubility, bioavailability, biological half-life, route of administration, product shelf life, as well as other pharmacological considerations can be contemplated by those preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The dosages can depend on many factors, and can in any event be determined by a suitable practitioner. Therefore, the dosages described herein are not intended to be limiting.

In some embodiments, the compositions further include an additional active ingredient. The preparation of a pharmaceutical composition that contains at least one compound or additional active ingredient can be known to those of skill in the art in light of the present disclosure, as exemplified by Remington's Pharmaceutical Sciences, 2003, incorporated herein by reference. Moreover, for animal (e.g., human) administration, it can be understood that preparations should meet sterility, pyrogenicity, and general safety and purity standards as required by the FDA Office of Biological Standards.

Packaging of the Composition

After formulation, the composition is packaged in a manner suitable for delivery and use by an end user. In one embodiment, the composition is placed into an appropriate dispenser and shipped to the end user. Examples of final container may include a pump bottle, squeeze bottle, jar, tube, capsule or vial.

The compositions and methods described herein can be embodied as parts of a kit or kits. A non-limiting example of such a kit comprises the ingredients for preparing a composition, where the containers may or may not be present in a combined configuration. In certain embodiments, the kits further comprise a means for administering the composition, such as a topical applicator, or a syringe. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A pharmaceutical composition for topical administration comprising:

an FSP27 fragment, wherein the FSP27 fragment consists of SEQ ID NO: 7; and a penetration enhancer comprising laurocapram.

2. The pharmaceutical composition of claim 1, wherein the pharmaceutical composition is selected from the group consisting of an ointment, a paste, a cream, and a powder.

3. The pharmaceutical composition of claim 1, further comprising one or more additional agents selected from the group consisting of emulsifiers, gelling agents, and antimicrobial preservatives.

4. The pharmaceutical composition of claim 1, further comprising an additional agent selected from the group consisting of an excipient, a diluent, and a carrier.

* * * * *

SEQUENCE LISTING

```
Sequence total quantity: 17
SEQ ID NO: 1            moltype = AA  length = 60
FEATURE                 Location/Qualifiers
source                  1..60
                        mol_type = protein
                        organism = synthetic construct
                        note = Description of Artificial Sequence: Synthetic
                         polypeptide
SEQUENCE: 1
MEYAMKSLSL LYPKSLSRHV SVRTSVVTQQ LLSEPSPKAP RARPCRVSTA DRSVRKGIMA  60

SEQ ID NO: 2            moltype = AA  length = 48
FEATURE                 Location/Qualifiers
source                  1..48
                        mol_type = protein
                        organism = synthetic construct
                        note = Description of Artificial Sequence: Synthetic
                         polypeptide
SEQUENCE: 2
YDLHCCGAKR IMKEAFRWAL FSMQATGHVL LGTSCYLQQL LDATEEGQ              48

SEQ ID NO: 3            moltype = AA  length = 81
FEATURE                 Location/Qualifiers
source                  1..81
                        mol_type = protein
                        organism = synthetic construct
                        note = Description of Artificial Sequence: Synthetic
                         polypeptide
SEQUENCE: 3
PRARPCRVST ADRSVRKGIM AYSLEDLLLK VRDTLMLADK PFFLVLEEDG TTVETEEYFQ  60
ALAGDTVFMV LQKGQKWQPP S                                            81

SEQ ID NO: 4            moltype = AA  length = 21
FEATURE                 Location/Qualifiers
source                  1..21
                        mol_type = protein
                        organism = synthetic construct
                        note = Description of Artificial Sequence: Synthetic peptide
SEQUENCE: 4
SEQGTRHPLS LSHKPAKKID V                                            21

SEQ ID NO: 5            moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 5
QQLLDATEEG Q                                                       11

SEQ ID NO: 6            moltype = AA  length = 29
FEATURE                 Location/Qualifiers
source                  1..29
                        mol_type = protein
                        organism = synthetic construct
                        note = Description of Artificial Sequence: Synthetic peptide
SEQUENCE: 6
QQLLDATEEG QPPKGKASSL IPTCLKILQ                                    29

SEQ ID NO: 7            moltype = AA  length = 119
FEATURE                 Location/Qualifiers
source                  1..119
                        mol_type = protein
                        organism = synthetic construct
                        note = Description of Artificial Sequence: Synthetic
                         polypeptide
SEQUENCE: 7
SEQGTRHPLS LSHKPAKKID VARVTFDLYK LNPQDFIGCL NVKATFYDTY SLSYDLHCCG  60
AKRIMKEAFR WALFSMQATG HVLLGTSCYL QQLLDATEEG QPPKGKASSL IPTCLKILQ   119

SEQ ID NO: 8            moltype = AA  length = 11
```

-continued

```
FEATURE                Location/Qualifiers
source                 1..11
                       mol_type = protein
                       organism = synthetic construct
                       note = Description of Artificial Sequence: Synthetic peptide
SEQUENCE: 8
SEQGTRHPLS L                                                 11

SEQ ID NO: 9           moltype = AA  length = 91
FEATURE                Location/Qualifiers
source                 1..91
                       mol_type = protein
                       organism = synthetic construct
                       note = Description of Artificial Sequence: Synthetic
                        polypeptide
SEQUENCE: 9
SEQGTRHPLS LSHKPAKKID VARVTFDLYK LNPQDFIGCL NVKATFYDTY SLSYDLHCCG  60
AKRIMKEAFR WALFSMQATG HVLLGTSCYL Q                           91

SEQ ID NO: 10          moltype = AA  length = 101
FEATURE                Location/Qualifiers
source                 1..101
                       mol_type = protein
                       organism = synthetic construct
                       note = Description of Artificial Sequence: Synthetic
                        polypeptide
SEQUENCE: 10
SEQGTRHPLS LSHKPAKKID VARVTFDLYK LNPQDFIGCL NVKATFYDTY SLSYDLHCCG  60
AKRIMKEAFR WALFSMQATG HVLLGTSCYL QQLLDATEEG Q                101

SEQ ID NO: 11          moltype = AA  length = 71
FEATURE                Location/Qualifiers
source                 1..71
                       mol_type = protein
                       organism = synthetic construct
                       note = Description of Artificial Sequence: Synthetic
                        polypeptide
SEQUENCE: 11
VARVTFDLYK LNPQDFIGCL NVKATFYDTY SLSYDLHCCG AKRIMKEAFR WALFSMQATG  60
HVLLGTSCYL Q                                                 71

SEQ ID NO: 12          moltype = AA  length = 238
FEATURE                Location/Qualifiers
source                 1..238
                       mol_type = protein
                       organism = Homo sapiens
SEQUENCE: 12
MEYAMKSLSL LYPKSLSRHV SVRTSVVTQQ LLSEPSPKAP RARPCRVSTA DRSVRKGIMA  60
YSLEDLLLKV RDTLMLADKP FFLVLEEDGT TVETEEYFQA LAGDTVFMVL QKGQKWQPPS  120
EQGTRHPLSL SHKPAKKIDV ARVTFDLYKL NPQDFIGCLN VKATFYDTYS LSYDLHCCGA  180
KRIMKEAFRW ALFSMQATGH VLLGTSCYLQ QLLDATEEGQ PPKGKASSLI PTCLKILQ    238

SEQ ID NO: 13          moltype = AA  length = 239
FEATURE                Location/Qualifiers
source                 1..239
                       mol_type = protein
                       organism = Mus sp.
SEQUENCE: 13
MDYAMKSLSL LYPRSLSRHV AVSTAVVTQQ LVSKPSRETP RARPCRVSTA DRKVRKGIMA  60
HSLEDLLNKV QDILKLKDKP FSLVLEEDGT IVETEEYFQA LAKDTMFMVL LKGQKWKPPS  120
EQRKKRAQLA LSQKPTKKID VARVTFDLYK LNPQDFIGCL NVKATLYDTY SLSYDLHCYK  180
AKRIVKEMLR WTLFSMQATG HMLLGTSSYM QQFLDATEEE QPAKAKPSSL LPACLKMLQ   239

SEQ ID NO: 14          moltype = AA  length = 246
FEATURE                Location/Qualifiers
source                 1..246
                       mol_type = protein
                       organism = Macaca mulatta
SEQUENCE: 14
MGSLRKGFGL LKDPWERAGF DWAACLRVSV RTSVVTQQLL SEPSPEAPRA RPCRVSTADR  60
SVRKGIMAYS LEDLLLKVRD TLMLADKPFF LVLEEDGTTV ETEEYFQALA GDIVFMVLQK  120
GQKWQPPSEQ GTRHPQSLSH KPAKKIDVAR VTFDLYKLNP QDFIGCLNVK ATFYDTYSLS  180
YDLHCCGAKR IVKEALRWAL FSMQATGHVM LGTSCYLQQL LDATEEGQPP KGKASSLIPT  240
CLRILQ                                                       246

SEQ ID NO: 15          moltype = AA  length = 238
FEATURE                Location/Qualifiers
source                 1..238
                       mol_type = protein
```

-continued

```
                        organism = Canis lupus
                        note = Canis familiaris
SEQUENCE: 15
MEYAMKSLSL LYPKSLSRHV AVSTSVVTQQ LSSKSSLEAP KARPCRVSTA DRSVRKGIIA  60
HSLKDLLNKV RDTLLLADKP FYLVLEEDGT TVETEEYFQA LADDTVFMVL QKGQKWQPPQ  120
EQGSRYQLSL SHKPAKKIDV AQVTFDLYKM NPQDFIGCLN VKATLYGTYS LSYDLHCYGA  180
KRIMKEVLRW ALFSMKTTGH VLLGTSCYMQ QLLDATEGGQ PPEGKARSLI PTSLKMLQ    238

SEQ ID NO: 16           moltype = AA  length = 222
FEATURE                 Location/Qualifiers
source                  1..222
                        mol_type = protein
                        organism = Bos taurus
SEQUENCE: 16
MAMYTAVSTS VVTQQQLSEP SAEAPRARPC RVTTADRSVR KGIMVHSLED LHVKVQDTLM  60
LAYRPFFLVL EEDGTTVETE EYFQSLADDT VFMVLHKGQK WQPPSEQSTR YQLALSHKPA  120
KIDVAQVTFD LYKVNPQDFI GCLNVKATLY GTYSVSYDLH CSGAKRIMKE ALRWALFSMR  180
TTGHMLLGTS CYLQQLLDAT EREQPPKSKA ASLIPTSLKM LQ                   222

SEQ ID NO: 17           moltype = AA  length = 236
FEATURE                 Location/Qualifiers
source                  1..236
                        mol_type = protein
                        organism = Xenopus sp.
SEQUENCE: 17
MEYAMKSLSL LSPKSLTKCV SVSASMTQQL LSRPVSKPRP FRVCNSNRSL RKGIVANSLE  60
DLINKTQDAL LMLEAITLVL DEDGTCVDTE EFFRSLDDGA VFMALAKGQK WKPTENSGYH  120
LSLTKKPARK IDVACVSFDL YKNHPRDFIG CLNVKATLYG TYSLSYDLQC YGAKRMVKEA  180
LRWTLYTMQA TGHVLLGTSC YMKQLLDATE RPVTEEEKSS TTLRDFIPFS PWKMLQ     236
```